US005618528A

United States Patent [19]
Cooper et al.

[11] Patent Number: 5,618,528
[45] Date of Patent: Apr. 8, 1997

[54] BIOLOGICALLY COMPATIBLE LINEAR BLOCK COPOLYMERS OF POLYALKYLENE OXIDE AND PEPTIDE UNITS

[75] Inventors: Eugene R. Cooper, Berwyn, Pa.; Stephen P. Jones, Morpeth, United Kingdom; Colin W. Pouton, Bristol, United Kingdom; Michael D. Threadgill, Bath, United Kingdom

[73] Assignee: Sterling Winthrop Inc., New York, N.Y.

[21] Appl. No.: 203,106

[22] Filed: Feb. 28, 1994

[51] Int. Cl.$^6$ ............................. A61K 47/42; C08G 81/00
[52] U.S. Cl. .................. 424/78.3; 525/54.1; 525/423; 525/430; 424/78.38
[58] Field of Search .................. 424/78.38, 78.3, 424/78.17; 525/54.1, 423, 430

[56] References Cited

U.S. PATENT DOCUMENTS

| | | | |
|---|---|---|---|
| 3,441,526 | 4/1969 | Zilkha et al. | 260/9 |
| 4,179,337 | 12/1979 | Davis et al. | 435/181 |

FOREIGN PATENT DOCUMENTS

| | | |
|---|---|---|
| WO92/00748 | 1/1992 | European Pat. Off. |
| WO93/02712 | 2/1993 | European Pat. Off. |
| 1469472 | 4/1977 | United Kingdom |

OTHER PUBLICATIONS

Guillermo Tous et al., "O'-(Epoxyalkyl) tyrosines and (Epoxyalkyl) phenylalanine as Irreversible Inactivators of Serine Proteases . . . ", J. Med. Chem. 1990, 33, 1620–1634.

M. Yokoyama et al., "Stabilization of Disulfide Linkage in Drug–Polymer–Immunoglobulin Conjugate by Microenvironmental Control", Biochemical & Biophysical Res. Comm., vol. 164, No. 3, 1989, pp. 1234–1239.

M. Yokoyama et al., "Preparation of Micelle–Forming Polymer–Drug Conjugates", Bioconjugate Chem. 1992, 3, 295–301.

Database WPI, AN 91–230961 and DD–287949, Section Ch, Week 9132, Derwent Publications Ltd., London, GB, Class 96, 14 Mar. 1991.

I N Topchieva et al., "The Interaction of Block Copolymers of Ethylene Oxide and Propylene Oxide and Their Polymer –Protein Conjugates with Lipids", Biomedical Sci. 1991, vol. 2, pp. 562–568.

W. Rapp et al., "Comparative Study of Antibody Titers induced by a Peptide Epitope . . . ", Peptides, 1990, pp. 849–850.

G. P. Kirillova, et al., "The Influence of Pluronics and thier Conjugates with Proteins on the Rate of Oxygen Consumption by Liver . . . ", Biotechnol. Appl. Biochem. 18, 329–339 [1993].

N. V. Efremova et al., "Conjugates of a–chymotrypsin with Polyalkylene Oxides", Moscow University, Chemistry Bulletin, vol. 47, No. 6, pp. 75–79, 1992.

N.V. Efremova et al., "Supramolecular Structures based on Protein Conjugates with Polyalkylene Oxides: B–cyclodextrin Complexes", School of Chemistry, vol. 58, No. 7, pp. 1071–1076, Jul. 1993.

Nathen et al., Bioconjugate Chemistry 454–62 (1993).

*Primary Examiner*—Edward J. Webman
*Attorney, Agent, or Firm*—Fish & Richardson PC

[57] ABSTRACT

A linear block copolymer comprising units of an alkylene oxide, linked to units of peptide via a linking group comprising a —$CH_2CHOHCH_2N(R)$— moiety, is useful as an imaging agent, drug, prodrug or as a delivery system for imaging agents, drugs or prodrugs.

17 Claims, No Drawings

BIOLOGICALLY COMPATIBLE LINEAR BLOCK COPOLYMERS OF POLYALKYLENE OXIDE AND PEPTIDE UNITS

BACKGROUND OF THE INVENTION a) Field of the Invention

This invention relates to block copolymers useful in diagnostic imaging, drug delivery, and as drugs.

b) Information Disclosure Statement

Nathen et al, Bioconjugate Chemistry 4 54–62 (1993) discloses copolymers of lysine and polyethylene glycol prepared by reacting amino groups of lysine with activated ester derivatives of polyethylene glycol. The polymer is best described as a polyamide formed by $\epsilon$-amino and the $\alpha$-amino of lysine.

Davis et al., U.S. Pat. No. 4,179,337 dated Dec. 18, 1979 discloses insulin coupled to polyethylene glycol or polypropylene glycol having a molecular weight of 500 to 20,000 molecular weight.

Zilkha et al, U.S. Pat. No. 3,441,526 issued Apr. 29, 1969 discloses N-carboxyanhydride-based polymerization of polypeptide with polyethylene glycol, no examples of the preparation are given.

British Patent 1,469,472 discloses low molecular weight polyethylene oxide immobilized proteins, said to have low immunogenicity.

However, none of these references suggests a linear block copolymer having repeating units of an alkylene oxide linked to repeating units of a peptide through a linking group formed by the reaction of an amine precursor and an epoxide precursor. Moreover, the prior art teaches that crosslinking (via amino acid side chains) often frustrates the linear copolymerization often sought. The invention described herein advantageously avoids such crosslinking.

SUMMARY OF THE INVENTION

The invention concerns a linear block copolymer comprising single or repeating units of poly(alkylene oxide) (PAG) linked to units of peptide. The copolymer can be tailored to produce water-soluble polymers which are stable in the blood circulation but ultimately will be degraded to allow more facile excretion of low molecular weight PAG derivatives in the urine.

In one aspect of the invention, the copolymer is a diagnostic agent, and/or a therapeutic agent and/or a targeting agent.

In another aspect of the invention, the copolymer is a chelating copolymer, having drug, and/or a prodrug and/or a chelating moiety attached to side chains of the peptide. Such moieties are useful in chelating metals, especially metals useful in diagnostic imaging of a body or tissues or as cytotoxic agents.

In another aspect the invention is a targeting delivery system for drugs and prodrugs.

In yet another aspect of the invention, the invention comprises the reaction of an epoxide and an amine to produce a novel polymer.

DETAILED DESCRIPTION INCLUSIVE OF PREFERRED EMBODIMENTS

We have discovered that linear block copolymers comprising blocks of poly(alkylene oxide) (PAGs) and peptides attached via —$CH_2CHOHCH_2N(R)$— based linking groups are useful as imaging agents, prodrugs, drugs and drug delivery systems. Preferred copolymers are of the formula;

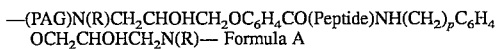
—(PAG)N(R)CH$_2$CHOHCH$_2$OC$_6$H$_4$CO(Peptide)NH(CH$_2$)$_p$C$_6$H$_4$ OCH$_2$CHOHCH$_2$N(R)— Formula A or

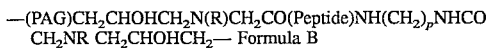
—(PAG)CH$_2$CHOHCH$_2$N(R)CH$_2$CO(Peptide)NH(CH$_2$)$_p$NHCO CH$_2$NR CH$_2$CHOHCH$_2$— Formula B wherein R is a 1–4 carbon alkyl; and p is from 1 to 6 and the peptide is preferably Gly-Phe-Leu-Gly or Lys-Gly-Phe-Leu-Gly.

The compounds can be tailored for specific uses by altering the size of the polymer or altering the peptide composition to provide differing blood pool residence time, enzymatic breakdown rates, and tissue distributions.

As an imaging agent, said composition preferably has a molecular weight of at least about 5000 and a metal ion useful as a contrast enhancer, fluorophore or x-ray opaque ion associated therewith, and thus suitable for use as an agent for diagnostic imaging.

An imaging metal is defined as a metal useful in x-ray imaging or a metal useful in magnetic resonance imaging, preferably a paramagnetic metal and more preferably a lanthanide metal or transition metal; or a metal useful in fluorescence imaging, preferably a lanthanide metal, most preferably Europium.

This invention further provides a method of performing a diagnostic imaging procedure in a body comprising administering to the body a contrast enhancing amount of the polymer described above, and then exposing the body to a magnetic resonance measurement step to image at least a portion of the body.

It is a particularly advantageous feature that the polymeric chelates of this invention provide effective imaging contrast enhancement of the blood pool within the vascular system for remarkably long periods of time.

It is another advantageous feature of this invention that polymeric compounds are provided having a specificity toward accumulation in different tissues, for example, in tumors and the liver.

As used herein, PAG refers to poly alkylene oxide moieties having a single type of repeating unit or differing (non-repeating) units of alkylene oxide, or a mixture thereof in each PAG. Each alkylene oxide unit in the PAG contains from 2 to about 4 carbons, linear or branched. Poly(alkylene oxide) units in the polymer may also differ in length and composition from each other. Exemplary PAG moieties include poly(ethylene oxides), poly(propylene oxides) and poly(butylene oxides). Preferred PAG moieties include poly(ethylene oxides), poly(propylene oxides) and random and block copolymers thereof. Poly(ethylene oxide)-containing polymers are particularly preferred when it is desired for the final polymer to possess solubility in water. It is also contemplated that the poly(alkylene oxide) moiety can comprise glycerol poly(alkylene oxide) triethers, polyglycidols, linear, block and graft copolymers of alkylene oxides with compatible comonomers such as poly(proplene oxide-co-ethylene oxide), or poly(butylene oxide-co-ethylene oxide) and grafted block copolymers. These moieties can be derived from poly(alkylene oxide) moieties which are commercially available or alternatively they can be prepared by techniques well known to those skilled in the art. A particularly preferred class of polyalkyleneoxide moieties derived from poly(ethylene oxide) can be represented by the structure:

—O(CH$_2$CH$_2$O)$_m$CH$_2$CH$_2$O— wherein m is 1 to 750. The preferred length depends upon the desired molecular weight.

These PAG moieties and their reactive derivatives, useful in preparing the polymer of the invention, are known in the art. For example, bis(methyl amino) polyethylene glycol and its use as an intermediate in the preparation of block copolymers is known in the art, for example; Mutter, Tetrahedron Letters, 31, 2839–2842 (1978) describes a procedure to convert the terminal hydroxyl groups of poly(ethyleneoxide) to reactive primary amino groups as well as the preparation of a number of reagents bound to poly(ethyleneoxide) amines; Harris et al, J. Polymer. Science, 22, 341–352 (1984) describe various PAG derivatives including for example, amino poly(ethyleneoxide). Other PAG derivatives are prepared by known chemistries examples of which are described hereinbelow.

As used herein, peptide refers to an amino acid chain of at least 2 amino acids, wherein each of the amino acids in the peptide may or may not be all the same, and may or may not all be selected from the 20 naturally occurring I-amino acids, but contain D-amino acids, artificial amino acids or amino acid derivatives, such as glutamate esters, lysyl(ε-amino)amides and the like. This definition also includes proteins, polypeptides and oligopeptides, which are art recognized amino acid chains. Specifically contemplated preferred peptides include small enzymes (less than 100 kd), peptide hormones, peptide recognition domains, peptide drugs, and peptides with known enzymatic breakdown rates.

Certain abbreviations appearing in the text and schemes are here defined: Boc refers to the art recognized t-butoxy carbonyl radical commonly used as a blocking agent in solid phase peptide synthesis. Conventional three letter abbreviations for amino acid residues are used throughout the specification. OPFP refers to pentafluorophenyloxy; Bn refers to benzyl; CBZ refers to phenylmethoxycarbonyl; OTCP refers to 2,4,5-trichlorophenyloxy; Troc refers to 2,2,2-trichloroethoxycarbonyl.

Copolymerization can occur by reaction of bis(oxiranyl)derivatives (also known as bis(epoxides)) with bis(amino or alkylamino) derivatives (also known as bis amines). There are no by-products of the polymerization reaction. The monomer units of PAG and peptide can be prepared as either bis(oxiranyl) derivatives or bis(amino) derivatives provided that the reaction producing the copolymers is between an amine and an epoxide. Therefore there are two chemical strategies for preparing products of the invention described hereinbelow. As a consequence of reacting bisamines with bisepoxides the sense of the PAG and peptide units can be reversed.

The polymer of the invention has between its PAG and peptide subunits, a linking group. The linking group contains a —CH$_2$CHOHCH$_2$N(R)— diradical, typically derived from the reaction of an amine and an epoxide. It is preferred that a bisepoxide subunit be reacted with a bisamine subunit. The skilled artisan will appreciate that the recitation used throughout the specification of each type of linking group diradical can be reversed and have the same meaning. Thus the sense of the linking group can be reversed (end for end), with one terminus attached to the PAG moiety, and the other terminus attached to the peptide or vise versa, while its recitation in the specification and the claims is the same.

Examples of suitable linking groups include
—CONH(CH$_2$)$_p$NHCOCH$_2$N(CH$_3$)CH$_2$CHOHCH$_2$OC$_6$H$_4$—;
—CONH(CH$_2$)$_p$NHCOCH$_2$N(CH$_3$)CH$_2$CHOHCH$_2$OC$_6$H$_4$CO—;
—CONH(CH$_2$)pNHCOCH$_2$N(CH$_3$)CH$_2$CHOHCH$_2$OC$_6$H$_4$(CH$_2$)$_2$—;
—CONH(CH$_2$)$_p$NHCOCH$_2$N(CH$_3$)CH$_2$CHOHCH$_2$OC$_6$H$_4$(CH$_2$)$_2$NH—;
—NH(CH$_2$)$_p$N(CH$_3$)CH$_2$CHOHCH$_2$OC$_6$H$_4$—;
—NH(CH$_2$)$_p$N(CH$_3$)CH$_2$CHOHCH$_2$OC$_6$H$_4$CO—;
—NH(CH$_2$)$_p$N(CH$_3$)CH$_2$CHOHCH$_2$OC$_6$H$_4$(CH$_2$)$_2$—;
—NH(CH$_2$)$_p$N(CH$_3$)CH$_2$CHOHCH$_2$OC$_6$H$_4$(CH$_2$)$_2$NH—;
—CONH(CH$_2$)$_p$NHCO(CH$_2$)pN(CH$_3$)CH$_2$CHOHCH$_2$—;
—NH(CH$_2$)$_p$NHCO(CH$_2$)pN(CH$_3$)CH$_2$CHOHCH$_2$—;
—NHCO(CH$_2$)$_p$N(CH$_3$)CH$_2$CHOHCH$_2$—; and
—CO(CH$_2$)$_p$N(CH$_3$)CH$_2$CHOHCH$_2$—.

Peptides used to prepare the invention can be prepared by standard procedures known in the art. Useful peptides include those derived from native or recombinant organisms, solid phase peptide synthesis or traditional wet chemistry peptide synthesis and the like. Each of these peptide preparation methods are well known in the art and use conventional, known materials. Protein expression and purification from natural and recombinant sources is in the prior art (cf. *Protein Expression and Purification* (1990); Harris et al., *Protein Purification Methods* (1989); Deutscher, M. P. *Guide to Protein Purification Methods in Enzymology*, Vol. 82 (1990)). Peptide synthesis is also known in the art (cf. Atherton, et al., *Solid Phase Peptide Synthesis a Practical Approach*, Oxford University Press (1989)). Thus, the peptides are easily prepared by known chemistry.

Linear peptide fragments can be tailored such that they are stable in blood, but are susceptible to lysosomal degradation by commonly occurring proteases. Examples of susceptible peptide units are gly-phe-leu-gly, gly-phe-tyr-ala, ala-gly-val-phe, gly-phe-ala-gly, and others known in the art. The prior art describes such oligopeptides as useful in preparing prodrugs, when the drug is attached to one terminus of the oligopeptide. (See generally "Polymers Containing Enzymatically Degradable Bonds" *Makromol. Chem.* 184 (1983) R. Duncan, H. C. Cable, J. B. Lloyd, P. Rejmanov'a and J. Kopecek, in Polymers containing enzymatically degradable bonds, 7. Design of oligopeptide sidechains to promote efficient degradation by lysosomal enzymes, *Makromol. Chem.*, 184, p. 1997–2008 (1983); and P. Rejmanova, J. Kopecek, J. Pohl, M. Baudys and V. Kostva, in Polymers containing enzymatically degradable bonds. 8. Degradation of oligopeptide sequences in N-(2-hydroxypropyl)methacrylamide copolymers by bovine spleen cathepsin B, *Makromol. Chem.* 184, p. 2009–2020, (1983).) In this invention it is contemplated that prodrugs can be attached to functionalized side chains of the peptide, rather than the terminus of the peptide.

The concept of drug targeting has gained importance in recent years, especially for anticancer drugs, inasmuch as toxic side effects of anticancer drugs to normal cells are a primary obstacle in cancer chemotherapy due to lack of selectivity of the anticancer drugs to cancer cells. In the prior art, drug targeting has been accomplished by drug conjugation with large antibodies, or encapsulation in a transporter specific to the target. Materials such as proteins, saccharides, lipids and synthetic polymers have been used for such transporters. Antibodies have been perhaps most widely used due to their target specificity and wide applicability. However, these methodologies have not been commercially exploited because the prohibitive cost of the transporter or targeting agent which can be used to target only one type of cell or tissue.

The peptide portion of the polymer can be tailored to recognize (or target) certain cells or functions of cells. Because the polymer can use more than one peptide and thus more than one type of peptide, the polymer can advantageously target more than one type of cell or tissue at once. Judicious choice of peptide allows treatment or targeting of more than one type of cancer cell, for example, or other disease state. This choice is facilitated by the prior art which contains a myriad of known oligopeptides which are antigenic to certain cells. Furthermore, the invention allows such targeting without the cost of raising antibodies to certain cells, harvesting such antibodies, conjugating antibodies to drug and further testing for maintained specificity after conjugation. The invention allows specific targeting to be achieved by short recognition sequences. Cell specific delivery can be achieved by incorporating targeting agents into the polymer. Preferred peptides are those which have a receptor molecule specific to a ligand of interest. Thus, a specific binding reaction involving the reagent can be used for the targeting expected.

Depending upon the intended use, the peptides can be selected from a wide variety of naturally occurring or synthetically prepared materials, including, for example enzymes, proteins, peptide hormones, virus coats, or proteins derived from blood components, tissue and organ components, including haptens, antibodies, antigenic proteinaceous materials, or fragments of any of these and others known to one skilled in the art.

Examples of these targeting peptides include: the integrin binding motif RGDS (arg-gly-asp-ser), which is present on many extracellular matrix proteins and can be used to interfere with cell adhesions involved in migration of leukocytes. Other peptide sequences which can be used to deliver the polymer include cationic sequences (ie. rich in lys or arg) which are useful in producing a DNA-binding polymer for use in supression of gene expression, antisense oligomer delivery and the like; peptide hormones such as αMSH which can be used for targeting to melanoma; and relatively low molecular weight (15–20 kDa) engineered hypervariable antibody binding domains ($V_H+V_L$ constructs) raised against any target. Such sequences are obtained by synthesis, isolation from cells or bacteriophages or they can also be raised against cells, proteins, or foreign substances in a host. Common hosts for raising recognition sequences include rabbits, goats, mice, and the like. These and other methods of obtaining recognition sequences are known in the art.

In certain embodiments, the above-described peptide can be an immunoreactive group, which would be found in a living organism or which finds utility in the diagnosis, treatment or genetic engineering of cellular material of living organisms. The peptide has a capacity for interaction with another component which may be found in biological fluids, cells or associated with cells to be treated or imaged, such as, for example tumor cells and the like.

Two highly preferred uses for the polymer of this invention are for the diagnostic imaging of tumors and the treatment of tumors. Preferred immunoreactive groups therefore include antibodies, or immunoreactive fragments thereof, to tumor-associated antigens. Specific examples include B72.3 antibodies (described in U.S. Pat. Nos. 4,522,918 and 4,612,282) which recognize colorectal tumors, 9.2.27 anti-melanoma antibodies, D612 antibodies which recognize colorectal tumors, UJ13A antibodies which recognize small cell lung carcinomas, NRLU-10 antibodies which recognize small cell lung carcinomas and colorectal tumors (Pan-carcinoma), 7E11C5 antibodies which recognize prostate tumors, CC49 antibodies which recognize colorectal tumors, TNT antibodies which recognize necrotic tissue, PR1A3 antibodies, which recognize colon carcinoma, ING-1 antibodies, which are known in the art and are described in International Patent Publication WO-A-90/02569, B174 antibodies which recognize squamous cell carcinomas, B43 antibodies which are reactive with certain lymphomas and leukemias and any other antibody which may be of particular interest.

Because the peptides of the polymer are linear, they can provide functional groups for coupling of diagnostic agents, drugs, or prodrugs or other targeting moieties by the side chains of individual amino acids found in the peptide portion of the backbone. Functional groups can also be added by reacting or derivatizing functionalizable basic groups (found for example in lysyl or argininyl residues) or acidic groups (as found in aspartate, glutamate, providing free carboxyl groups), or sulfhydryl groups, (e.g. cysteine), hydroxyl groups (such as found in serine) and the like. This coupling is done by standard peptide chemistry known in the art.

Cytotoxic drugs can also be coupled to the polymer to produce prodrugs which are released as a drug to targeted cells or tissues. Such coupling methods are known in the art, see for example; Duncan, P. Kopeckova-Rejmanova, J. Strohalm, I. Hume, H. C. Cable, J. Pohl, J. B. Lloyd and J. Kopecek (1987) Anti-cancer agents coupled to N-(2-hydroxypropyl)methacrylamide copolymers. I. Evaluation of daunomycin and puromycin conjugates in vitro. British J. Cancer, 55:165–174. R. Duncan, P. Kopeckova, J. Strohalm, I. Hume, J. B. Lloyd and J. Kopecek (1988) Anti-cancer agents coupled to N-(2-hydroxypropyl)methacrylamide copolymers. II. Evaluation of daunomycin conjugates in vivo against L1210 leukaemia. British J. Cancer, 57:147–156. Drugs contemplated to be useful include any drug which can be covalently attached to the polymer and retains its activity when so attached. It is contemplated that drugs which become active only when liberated from the polymer are also useful, and as such are prodrugs.

Drugs which are contemplated to be useful in the polymer include cytotoxic agents, and immunomodulating peptides and proteins as described above.

By "cytotoxic agent", it is meant any agent able to kill cells, including, chemotherapeutic agents such as cytotoxic drugs and cytotoxic antibiotics, chelated radionuclides and toxins or any agent which initiates or which leads to cell death. The term cytotoxic agents also includes agents which activate a host's immune response leading to cell death. The cytotoxic agent will be selected with reference to factors, such as the type of disease state, for example the type of cancer tumor and the efficacy of a certain chemotherapy agent for treating the cancer tumor involved, and the like. The cytotoxic agent may be selected from alkylating agents, antimetabolites, natural products useful as cytotoxic drugs, hormones and antagonists and other types of cytotoxic compounds.

Examples of alkylating agents include the nitrogen mustards (i.e. the 2-chloroethylamines) such as, for example, chloromethine, chlorambucil, melphalan, uramustine, mannomustine, extramustine phosphate, mechlor-thaminoxide, cyclophosphamide, ifosamide and trifosfamide; alkylating agents having a substituted aziridine group such as, for example, tretamine, thiotepa, triaziquone and mitomycin; alkylating agents of the alkyl sulfonate type, such as, for example, busulfan and piposulfan; alkylating N-alkyl-N-nitrosourea derivatives such as, for example, carmustine, lomustine, semustine or streptozotocine; alkylating agents of the mitobronitole, dacarbazine and procarbazine type; and platinum complexes such as, for example, cisplatin and carboplatin and others.

Examples of antimetabolites include folic acid derivatives such as, for example, methotrexate, aminopterin and 3'-dichloromethotrexate; pyrimidine derivatives such as, for example, 5-fluorouracil, floxuridine, tegafur, cytarabine, idoxuridine, and flucytosine; purine derivatives such as, for example, mercaptopurine, thioguanine, azathioprine, tiamiprine, vidarabine, pentostatin and puromycin and others.

Examples of natural products, useful as cytotoxic agents include for example vinca alkaloids, such as vinblastine and vincristine; epipodophylotoxins such as, for example, etoposide, and teniposide; antibiotics such as, for example, adrimycin, daunomycin, dactinomycin, daunorubicin, doxorubicin, mithramycin, bleomycin and mitomycin; enzymes such as, for example, L-asparaginase; biological response modifiers such as, for example, alpha-interferon; camptothecin; taxol; and retinoids such as retinoic acid and the like.

Examples of hormones and antagonists include adrenocorticoids, such as, for example, prednisone; progestins, such as, for example, hydroxyprogesterone acetate, medroxyprogesterone acetate and megestrol acetate; estrogens such as, for example, diethylstilbestrol and ethinyl estradiol; antiestrogens such as for example, tamoxifen; androgens such as, for example, testosterone propionate and fluoxymesterone; antiandrogens such as, for example, flutamide; and gonadotropin-releasing hormone analogs such as, for example, leuprolide.

Examples of miscellaneous cytotoxic agents include anthracenediones such as for example, mitoxantrone; substituted ureas such as, for example, hydroxyureas; and adrenocortical suppressants such as, for example, mitotane and aminoglutethimide. The cytotoxic agent can be ionically associated with the chelating residue. For example, in preferred embodiments, the cytotoxic agent is a radionuclide comprising a radioactive metal ion such as described below associated with a peptide-linked chelating residue. The polymer of the invention can contain one or more of a wide variety of chelating agents. As is well known, a chelating agent is a compound containing donor atoms that can combine by coordinate bonding with a cation to form a cyclic structure called a chelation complex or chelate. This class of compounds is described in the Kirk-Othmer Encyclopedia of Chemical Technology, Vol. 5, 339 –368.

Chelating residues may also be attached via the functionalizable side chains of the peptide via known chemistry. These chelating residues can be coupled to the polymer to produce contrast agents useful in diagnostic imaging or cytotoxic agents when complexed with the appropriate metal. The chelating residue is attached to an available amino acid side chain in the peptide portion of the polymer by a protein reacting group. By "protein reactive group" it is meant any group which can react with any functional groups typically found in proteins, especially an amino acid side chain.

Preferred protein reactive groups can be selected from but are not limited to:

(1) A group that will react directly with the amine or sulfhydryl groups on an amino acid side chain. For example, active halogen containing groups including, for example, chloromethylphenyl groups and chloroacetyl [Cl—CH$_2$CO—] groups, activated 2-leaving-group-substituted ethylsulfonyl and ethylcarbonyl groups such as 2-chloroethylsulfonyl and 2-chloroethylcarbonyl; vinylsulfonyl; vinylcarbonyl; epoxy; isocyanato; isothiocyanato; aldehyde; aziridine; succinimidoxycarbonyl; activated acyl groups such as carboxylic acid halides; mixed anhydrides and the like; and other groups known to be useful in attaching molecules to proteins or crosslinking proteins and the like.

(2) A group that can react readily with modified proteins or similar biological molecules modified to contain reactive groups such as those mentioned in (1) above, for example, by oxidation of the amino acid side chain to an aldehyde or a carboxylic acid, in which case the "protein reactive group" can be selected from amino, alkylamino, arylamino, hydrazino, alkylhydrazino, arylhydrazino, carbazido, semicarbazido, thiocarbazido, thiosemicarbazido, sulfhydryl, sulfhydrylalkyl, sulfhydrylaryl, hydroxy, carboxy, carboxyalkyl and carboxyaryl. The alkyl portions of the protein reactive group can contain from 1 to about 18 carbon atoms as described for R above. The aryl portions of the protein reactive group can contain from about 6 to about 20 carbon atoms.

(3) A group that can be linked to the amino acid side chain or similar biological molecule, or to the modified peptide as noted in (1) and (2) above by use of a crosslinking agent. Certain useful crosslinking agents, such as, for example, difunctional gelatin hardeners, bisisocyanates etc., which become a part of a linking group in the polymer during the crosslinking reaction. Other useful crosslinking agents, such as, for example, consumable catalysts, are not present in the final conjugate. Examples of such crosslinking agents are carbodiimide and carbamoylonium crosslinking agents as disclosed in U.S. Pat. No. 4,421,847 and the dication ethers of U.S. Pat. No. 4,877,724. With these crosslinking agents, one of the reactants must have a carboxyl group and the other an amine, alcohol, or sulfhydryl group. The crosslinking agent first reacts selectively with the carboxyl group, then is cleaved during reaction of the "activated" carboxyl group with, for example, an amine to form an amide linkage between the peptide portion of the polymer and metal complexing agents, thus covalently bonding the two moieties. An advantage of this approach is that crosslinking of like molecules, e.g., amino acid side chains with amino acid side chains or complexing agents with complexing agents is avoided, whereas the reaction of difunctional crosslinking agents is less selective. Especially preferred protein reactive groups include amino and isothiocyanato. Preferred chelating agent precursors have anhydride, sulfonylylchloride, alkylsulfate, vinyl sulfate, or ester functionalkyl.

The chelating residues can be .derived from chelating moieties which are selected to contain electron donating atoms which will chelate a metal, by forming coordination bonds therewith. These moieties can be selected from polyphosphates, such as sodium tripolyphosphate and hexametaphosphoric acid;

aminocarboxylic acids, such as ethylenediaminetetra-acetic acid, N-(2-hydroxyethyl)ethylenediaminetriacetic acid, nitrilotriacetic acid, N,N-di(2-hydroxyethyl)glycine, ethylenebis(hydroxyphenylglycine) and diethylenetriamine pentaacetic acid;

1,3-diketones, such as acetylacetone, trifluoroacetylacetone, and thenoyltrifluoroacetone;

hydroxycarboxylic acids, such as tartaric acid, citric acid, gluconic acid, and 5-sulfosalicylic acid;

polyamines, such as ethylenediamine, diethylenetriamine, triethylenetetramine, and triaminotriethylamine;

aminoalcohols, such as triethanolamine and N-(2-hydroxyethyl)ethylenediamine;

aromatic heterocyclic bases, such as 2,2'-dipyridyl, 2,2'-diimidazole, dipicoline amine and 1,10-phenanthroline;

phenols, such as salicylaldehyde, disulfopyrocatechol, and chromotropic acid;

aminophenols, such as 8-hydroxyquinoline and oxinesulfonic acid;

oximes, such as dimethylglyoxime and salicylaldoxime;

peptides containing proximal chelating functionality such as polycysteine, polyhistidine, polyaspartic acid, polyglutamic acid, or combinations of such amino acids;

Schiff bases, such as disalicylaldehyde 1,2-propylenedimine;

tetrapyrroles, such as tetraphenylporphin and phthalocyanine;

sulfur compounds, such as toluenedithiol, meso-2,3-dimercaptosuccinic acid, dimercaptopropanol, thioglycolic acid, potassium ethyl xanthate, sodium diethyldithiocarbamate, dithizone, diethyl dithiophosphoric acid, and thiourea;

synthetic macrocylic compounds, such as dibenzo[18]crown-6, $(CH_3)_6$-[14-]4,11-diene-$N_4$, and (2.2.2)-cryptate; and phosphonic acids, such as nitrilotrimethylenephosphonic acid, ethylenediaminetetra(methylenephosphonic acid), and hydroxyethylidenediphosphonic acid, or combinations of two or more of the above agents.

Preferred chelating residues contain polycarboxylic acid or carboxylate groups and include elements present in: ethylenediamine-N, N, N',N'-tetraacetic acid (EDTA); N,N,N',N'',N''-diethylenetriaminepentaacetic acid (DTPA); 1,4,7,10-tetraazacyclododecane-N,N',N'',N'''-tetraacetic acid (DOTA); 1,4,7,10-tetraazacyclododecane-N,N',N''-triacetic acid (DO3A); 1-oxa-4,7,10-triazacyclododecane-N,N',N''-triacetic acid (OTTA); trans(1,2)-cyclohexanodiethylenetriamine pentaacetic acid (CDTPA);

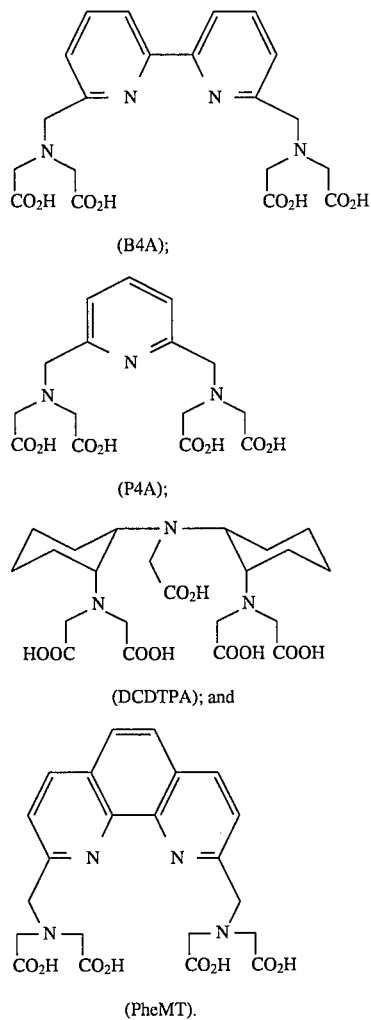

(B4A);

(P4A);

(DCDTPA); and (PheMT).

Such chelating compounds, including their preparation and manipulation are well known in the art. For example, the acid and anhydride forms of EDTA and DTPA are commercially available; methods for preparing B4A, P4A and TMT are described in U.S. Pat. No. 4,859,777; the disclosure of which is hereby incorporated by reference; and other suitable chelating groups are known in the art, and are described in PCT/US91/08253, and many other readily available references.

If the chelating residue is made of multiple chelating moieties or subunits, such subunits can be linked together by a linking group. Thus, more than one chelating moiety can be used to make up the chelating residue. If more than one chelating moiety is present in the chelating residue, these may be the same or different. Chelating moieties can be linked together using known chemistries. Thus the chelating residue can be one moiety or a "core" of chelating moieties. For example, a core of DTPA residues may be prepared by reacting DTPA dianhydride with a aliamine, such as ethylene diamine, to form a "core" of DTPA chelators. Other chelating residues, made up of multiple chelating moieties are well known in the art and are prepared by known chemistries as well.

For magnetic resonance imaging applications, $M^{(+a)}$ preferably represents a paramagnetic metal ion such as an ion of metals of atomic number 21 to 29, 42, 44 and 57 to 71, especially 57 to 71. Ions of the following metals are preferred: Cr, V, Mn, Fe, Co, Ni, Cu, Ce, Pr, Nd, Pro, Sin, Eu, Gd, Tb, Dy, Ho, Er, Tm and Yb. Especially preferred are $Cr^{+3}$, $Cr^{+2}$, $V^{+2}$, $Mn^{+3}$, $Mn^{+2}$, $Fe^{+3}$, $Fe^{+2}$, $Co^{+2}$, $Gd^{+3}$ and $Dy^{+3}$. It is a particularly advantageous feature that polymers can be provided exhibiting a high substitution ratio, i.e., containing relatively large numbers of paramagnetic metal ions per molecule.

The cytotoxic agent can be a radioactive isotope, preferably a radioactive metal ion isotope. This radioactive metal isotope can be an ion of an isotope of a metal selected, for example, from Sc, Fe, Pb, Ga, Y, Bi, Mn, Cu, Cr, Zn, Ge, Mo, Tc, Ru, In, Sn, Re, Sr, Sin, Lu, Du, Sb, W,, Re, Po, Ta and Tl ions. In a prefered embodiment, radioisotopes which are also useful in diagnostic imaging applications are specifically contemplated. Thus this embodiment finds utility in imaging and therapy where either procedure can be performed in conjunction with or ancillary to the other. Preferred isotopes of radioactive metal ions for this embodiment include $^{44}Sc$, $^{64,67}Cu$, $^{111}In$, $^{212}Pb$, $^{68}Ga$, $^{90}Y$, $^{153}Sm$, $^{212}Bi$, $^{99m}Tc$ and $^{188}Re$ for therapeutic and diagnostic imaging applications.

If a metal is chelated by the polymer, as for example, in imaging or therapy as described above, the metal content in the polymer can vary from about 0.1 up to about 20% based on the total weight of the polymer. For example in a magnetic resonance imaging embodiment, the polymer preferably contains a paramagnetic metal ion in an amount of from 1 to 25%, more preferably 2–20% by weight. In a therapeutic embodiment the radionuclide metal ion is present in roughly the same amounts as for imaging.

The PAG moiety in this composition can be capped at the terminus with a capping moiety selected from a hydrogen, hydroxy, alkyl, amine, or alkoxy. Preferred capping groups are hydrogen or hydroxyl groups. Thus capping is done by known chemistry, and precapped prepolymers are available. It is further contemplated that cyclic copolymers can be prepared.

The compositions of this invention can be prepared in water-soluble, water-dispersible or water-insoluble forms depending upon the intended application. The composition can have a molecular weight ranging from 10,000 to 1 million preferably 11,000 to 80,000. The preferred molecular weight varies according to the application as described below.

In addition to targeted delivery of the polymers of the invention, the polymer can be selectively delivered to specific cells, tissue types, or organs with or without the aid of a targeting agent. When no targeting agent is used such targeted delivery is based on size (hydrodynamic radius) and charge alone. The charge of the polymer can be altered by judicious choice of the aminoacids used in the peptide component of the copolymer to suit the application. Of course, the size of the polymer can be chosen by altering the size of PAG or peptide used to prepare the polymer or by altering the degree of polymerization. The mechanism of the targeted delivery of polymer is thought to be based upon the passive biodistribution in tissues of the polymer. It is thought that this passive biodistribution can occur because the PAG component of the polymers allows free distribution of the polymers within the circulatory system, with low antigenicity or without interference by the mononuclear phagocytic system. Unlike hydrophobic polymers known in the art, which are taken up by the reticuloendothelial system, the polymers of the invention can be designed to be distributed to tissues without being metabolized. Thus the size and charge of the polymer in the tissue is a function of the size and charge of the polymer administered. Distribution of the unmetabolized polymer to tissues will be influenced by the nature of the local vascular endothelium in each tissue and the prescence or absence of a lymphatic system. Three general categories of vascular endothelium are sinusoidal epithelium, characterized by discontinuity and little or no basement membrane; fenestrated vascular endothelium; and continuous vascular endothelium, characterized by tight junctions and basement membrane. The lymphatic system is known to recirculate proteins and other molecules which can float freely in the plasma, but escape the circulatory system, exist for a time in tissue and then are returned to the circulatory system via the lymphatic system. The skilled artisan can determine which tissues will be passively targeted by the polymer by approximating the molecular weight or more preferably the hydrodynamic radius of known proteins diffusing through the tissue in a known given period.

Tissues such as bone marrow, liver and spleen tissue are characterized by sinusoidal endothelium, (which allows escape of large molecules from the circulating system into the surrounding tissue) thus larger polymer molecules are useful in passively targeting such tissues. Tissues such as found in the GI tract, kidney glomeruli, and endocrine gland tissue are characterized by fenestrated endothelium (which allows escape of smaller macromolecules from the circulatory system), thus slightly smaller polymer molecules are useful in passively targeting such tissues. Tissues such as muscle and lung tissue are characterized by continuous vascular endothelium (which allows small molecules to escape from the circulatory system into the surrounding tissue), thus smaller polymer molecules are useful in passively targeting these tissues.

For example, the hydrodynamic radius of albumin is approximately 37 Å, its molecular weight is 67 Kd, and its charge is known. It is known that the average half life for albumin circulation through tissue is approximately 24 hours, but this half life is longer in some tissues and shorter in others. Moreover, the concentration of albumin in certain tissues is appreciable and in other tissues albumin is nearly absent altogether. The skilled artisan can prepare a polymer of approximately the same size, or preferably the same hydrodynamic radius and charge, and expect a similar half life and concentration in tissues.

The skilled artisan will recognize that inflammation of tissues will perturb the normal physiology of that tissue and thus the half life and concentration of macromolecules, such as proteins or the polymer of the invention, in an inflamed tissue or inflamed tissue site. Thus the polymer finds utility in imaging and/or treating such inflamed tissues or inflamed tissue sites.

The skilled artisan will also appreciate that the absence of a lymphatic system in a tissue will perturb the concentration and increase the half life of macromolecules in a tissue because no convenient mechanism is provided for the scavenging of such macromolecules. Such is the case in growing tumors. One can deliver a cytotoxic agent, a pro-drug, or an imaging moiety to the growing tumor surface based on size of the polymer and on vasculature of the surrounding targeted tissue as described above. Thus dosing a cytotoxic agent will result in accumulation of such agent in the growing surface of the tumor.

Thus molecular weight and charge of the polymer may be tailored to the specific application based on tissue type, presence or absence of inflammation, tumor and/or vasculature type and presence or absence of a lymphatic system to provide a polymer with the correct characteristics for targeting the desired tissue.

The general synthetic methods for production of linear alternating polymers follow two related schemes (A and B) involving the reaction of a bis-(methylamino)-monomer with a bis(oxiranyl)-monomer described below. Compounds of the invention are prepared by chemical transformations which are conventional and known to those skilled in the art of chemistry. Furthermore, known transformations can be used for effecting changes in functional groups in the polymer or compounds used in preparing the polymer of the invention. For example, acylation of hydroxy- or amino-substituted species to prepare the corresponding esters or amides, respectively; simple aromatic and heterocyclic substitutions or displacements; cleavage of alkyl or benzyl ethers to produce the corresponding alcohols or phenols; and hydrolysis of esters or amides to produce the corresponding acids, alcohols or amines, preparation of anhydrides, acid halides, aldehydes, simple aromatic alkylation and the like as desired can be carried out.

Such transformations will provide suitable chelating agents and precursors thereof containing reactive functionality, including, for example, polycarboxylic acids in dianhydride form, di(sulfonyl chlorides), di(alkyl sulfates), di(vinyl sulfones), diesters, and the like. Such known transformations are also useful in attaching the chelator to the polymer or polymer precursor, and in preparing the polymer itself. However, as will be recognized by one skilled in the art, obtaining the desired product by some reactions will be better facilitated by blocking or rendering certain functional groups inert. This practice is well recognized in the art, see for example, Theodora Greene, *Protective Groups in Organic Synthesis* (1991). Thus when reaction conditions are such that they may cause undesired reactions with other parts of the molecule, for example in portions of the chelator intended to become ligands, the skilled artisan will appreciate the need to protect these reactive regions of the molecule and will act accordingly. For example, the chelating residue containing reactive functionality can be prevented from reacting to form undesired products by suitably blocking the chelating residue precursor which can be contacted with the reactive poly(alkylene oxide) moiety to form the polymer, and then the blocking group can be subsequently removed by techniques known in the art. For example, if hydroxy substituents are to be selectively present in the final polymer, they preferably should be temporarily blocked during polymerization, such as by formation of an alkyl ether from the hydroxyl by conventional blocking techniques to minimize formation of undesirable by products. However, by products which contain one or more linkages formed by unblocked reactive precursor groups in the backbone of the polymer are contemplated to be useful.

Small proteins or peptides may be incorporated into the polymer by methods as described hereinbelow. An advantage of this chemistry is that the N and C terminus of the peptide can be reversed or randomized in the polymer of the invention, reducing immunogenicity or masking peptide activity until the peptide is liberated.

Scheme A

Bis-(oxiranyl)-peptide Monomers (Apep) are Reacted with bis-(alkylamino)-PAG Derivative Monomers (Apag)

A linking group precursor is added to the PAG monomers at the terminal hydroxy. The reaction of the known linking group precursor with the known PAG moiety forms a (PAG)-linking group precursor radical. The precursor radical is chosen from aminoalkylamino, N-sarcosyl-aminoalkyl-amino, or N-sarcosylaminoalkylamino-N'-carboxy.

In this scheme, the peptide monomers, have 4-(oxiranylmethoxy) aryl radicals connected as linking group precursors using carboxy funtionality to attach to the N terminus of the peptide or amino functionality to attach to the C terminus of the peptide, thus forming amide bonds with the N terminus with the C terminus of the peptide monomer with the one end of each linking group precursor, and having an oxirane at the other end of each linking group precursor as shown by the example below:

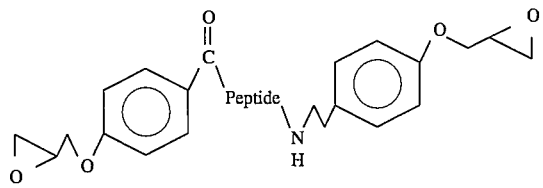

This oxirane functionalized peptide is referred to as Apep.

As an example Apep can be;

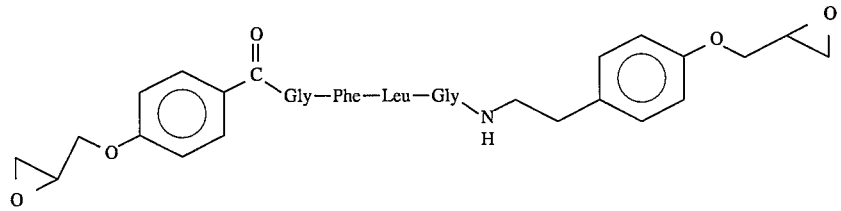

and is combined with Bis(amino)PAG monomers (Apag), such as:

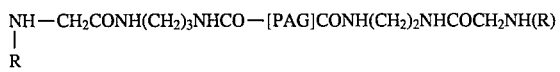

wherein R is lower alkyl.

Such PAG derivatives are prepared by known chemistry, for example; the preparation of an acid chloride from PAG monomers by SOCl$_2$, COCl$_2$ and the like, with subsequent reaction with a suitable diamine, or another suitable linking group, such as —N(R)CH$_2$CONHCH$_2$CH$_2$NH$_2$, or the like.

Scheme B

Alternatively, oxiranyl functionality can be used on PAG derivative monomers while using amino functionality on peptide derivative monomers. In this scheme, bis-(alkylamino)-peptide monomers (Bpep) are reacted with bis-(oxiranyl)-PAG monomers (Bpag). The peptide has a linking group precursor radical attached to the C and N termini so as to provide terminal amine functionality. Glycine or sarcosine can be used as the linking group precursor for the N terminus. The C terminus is attached to a —NH(CH$_2$)$_p$NHCOCH$_2$NH(R) or —NH(CH$_2$)$_p$NHCOCH$_2$NH$_2$ linking group precursor radical which is derived from a diamine (wherein P is one to six, R is an alkyl radical, linear or branched, of 1 to about 4 carbons) and glycine or sarcosine. Thus the peptide is attached to the linking group precursor via amide linkages at both the N and C termini.

An example of Bpep is:

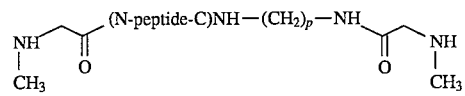

wherein p is 1 to about 6.

The bis(oxiranyl) PAG monomers (Bpag) of formula;

are known in the art. (See Y. Chen and M. Feng, Chinese Patent 86/104,089 (1987))

Thus it will be appreciated that the bis (alkylamine) and bis (oxiranyl) functionality may be on either the PAG moiety or the peptide moiety; so long as the polymerization takes place between a peptide and PAG, using the reaction of an amine and an epoxide.

Before, during or after polymerization, suitable chelating agents and precursors thereof may be attached to the polymer or polymer precursor. As described previously, a suitably blocked progenitor to the chelating agent or precursor thereof containing reactive functionality can be contacted with the reactive amino acid side chain incorporated into the polymer or polymer precursor to form the chelate-polymer or chelate polymer precursor, and then any blocking groups can be subsequently removed by techniques known in the art, thus avoiding formation of undesired by products.

The metallized polymer can be formed by contacting the unmetallized polymer sequentially or simultaneously with one or more sources of metal ions. This can be conveniently accomplished by adding one or more metal ion solutions or one or more metal ion solid salts or metal ion oxides, preferably sequentially, to a solution, preferably an aqueous solution, of the polymer. Thereafter, or between sequential addition of metal ions, the chelated polymer preferably is diafiltered in water to remove excess unbound metal.

The composition preferably is prepared in a water soluble, for example, an injectable form when used as magnetic resonance contrast agent for blood pool imaging, as a composition intended to be administered intravenously, and the like. The preparation of water-soluble compositions of molecular weight 10,000 to 50,000 can be accomplished by known methods by one skilled in the art.

The following example illustrates the preparation of an example of a compound of formula A. It is understood that the example presented does not limit the claims or invention claimed.

Example A

The synthesis of the compound prepared by Method A, giving a compound of formula A is achieved according to the following scheme;

Preparation of the Peptide Portion of Example A

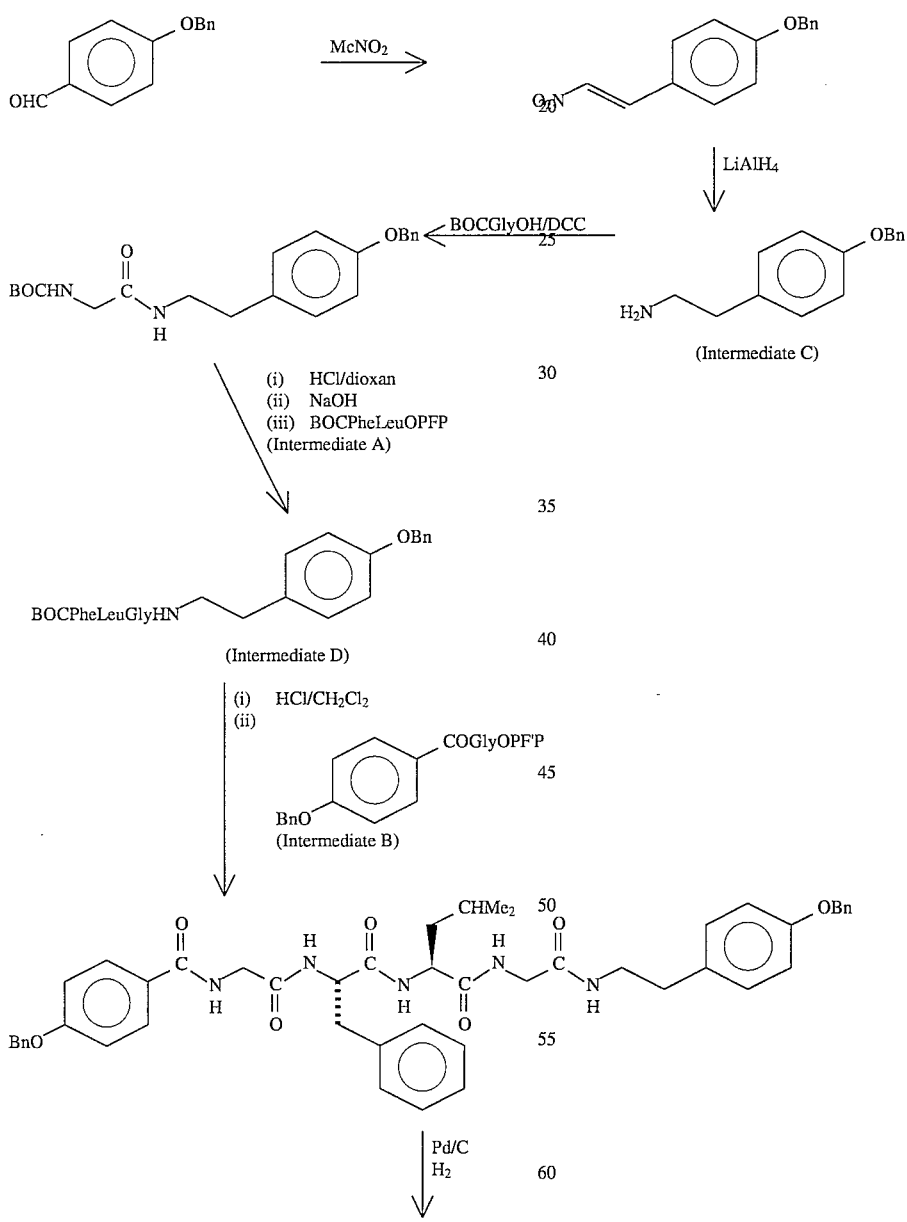

Preparation of the Peptide Portion of Example A (Cont.)

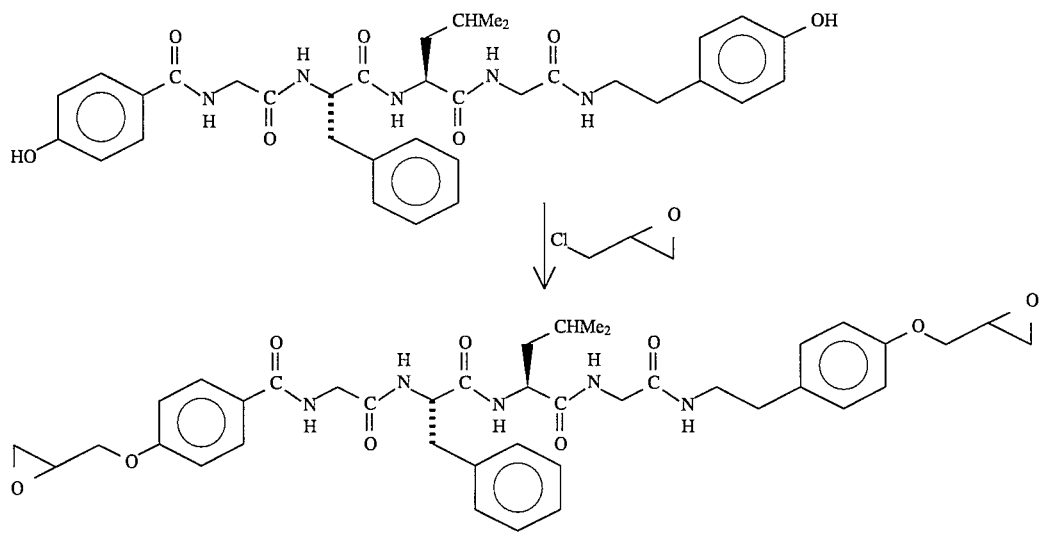

Preparation of PAG Portion of Example A

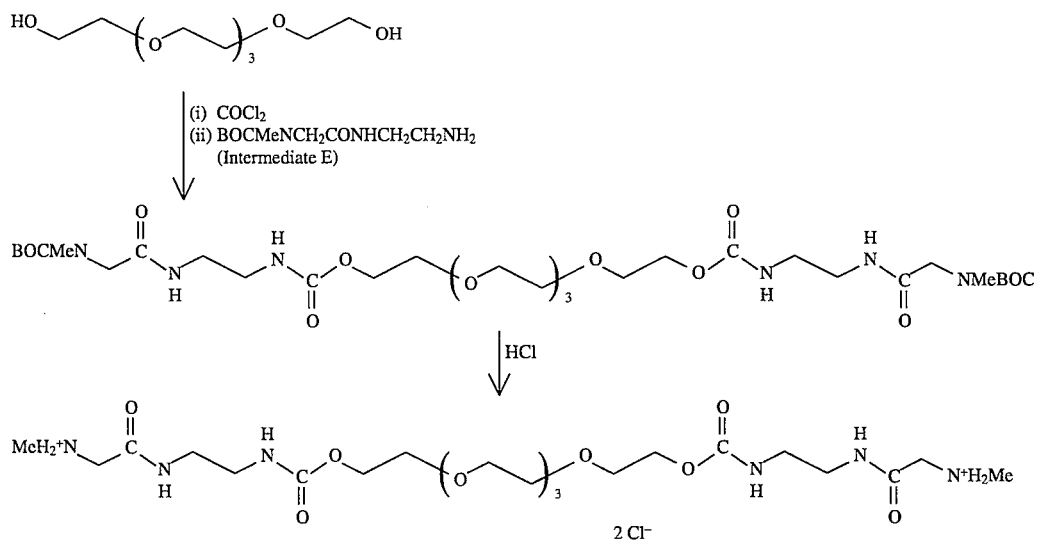

EXAMPLE A

Intermediate A

1. N-(N-(1,1-Dimethylethoxycarbonyl)phenylalanyl)leucine pentafluorophenylester. N-(N-(1,1-Dimethylethoxycarbonyl)-phenylalanyl)leucine (23.0 g, 61 mmol) (prepared by a literature method[Anderson, G. W.; McGregor, A. C., t-Butoxycarbonyl amino acids and their use in peptide synthesis, J. Am. Chem. Soc., 1957, 79, 6180–6183]) was stirred with pentafluorophenol (11.2 g, 61 mmol) and dicyclohexylcarbodilmide (12.5 g, 61 mmol) in tetrahydrofuran (170 mL) for 1 h at 0° C. The suspension was filtered. The solvent was evaporated from the filtrate under reduced pressure. The residue, in dichloromethane, was washed twice with saturated aqueous sodium hydrogen carbonate and with water. The solution was dried with anhydrous magnesium sulphate and the solvent was evaporated under reduced pressure to give N-(N-(1,1-dimethylethoxycarbonyl)phenylalanyl)leucine pentafluorophenyl ester (28.0 g, 85%).

Intermediate B 1. 4-(Phenylmethoxy)benzoic acid. In a modification of the literature method [E. L. Elied, R. P. Anderson, Reactions of esters with targeting amines. I. Benzyl esters from methyl esters and benzyldimethylamine, J. Am. Chem. Soc., 1952, 74, 547–549] a mixture of 4-hydroxybenzoic acid (27.6 g, 200 mmol), chloromethylbenzene (57.0 g, 450 mmol), potassium carbonate (50 g) and sodium iodide (25 g) was boiled under reflux in acetonitrile (500 mL) for 16 h. The suspension was filtered and the solvent was evaporated from the filtrate under reduced pressure. The residue was recrystallised from ethanol to give phenylmethyl 4-(phenylmethoxy)benzoate (48.8 g, 76%). Phenylmethyl 4-(phenylmethoxy)benzoate (48.8 g, 150 mmol) was boiled under reflux with aqueous sodium hydroxide (2M; 250 mL) and ethanol (250 mL) for 4 h. The ethanol was evaporated under reduced pressure. Water (1000 mL) was added. The white solid was collected by filtration, warmed to 65° C. with aqueous sulphuric acid (2M; 300 mL) for 1 h and extracted with warm ethyl acetate. The ethyl acetate solution was dried with anhydrous magnesium sulphate and the solvent was evaporated under reduced pressure to give 4-(phenylmethoxy)benzoic acid (27.15 g, 80%). The filtrate was washed twice with diethyl ether, acidified by addition of sulphuric acid (2M) and extracted with diethyl ether. Evaporation of the diethyl ether gave a further portion of 4-(phenylmethoxy)benzoic acid (6.0 g, 18%). The total yield was 98%.

2. 4-(Phenylmethoxy)benzoyl chloride. 4-(Phenylmethoxy)benzoic acid (500 mg, 2.2 mmol) was stirred with oxalyl chloride (280 mg, 2.2 mmol) and dimethylformamide (25 mg) in 1,4-dioxan (25 mL) for 20 min. The solvent and catalyst were evaporated under reduced pressure. The residue was recrystallised from hexanes to give 4-(phenylmethoxy)benzoyl chloride (460 mg, 85%).

3. N-(4-(Phenylmethoxy)benzoyl)glycine methyl ester. 4-(Phenylmethoxy)benzoyl chloride (13.64 g, 55.5 mmol) in dichloromethane (90 mL) was added dropwise to glycine methyl ester hydrochloride (7.66 g, 61 mmol) and triethylamine (11.78 g, 116.5 mmol) in dichloromethane (250 mL). The mixture was stirred for 16 h. The suspension was filtered. The solvent was evaporated from the filtrate under reduced pressure. The residue was recrystallised from dichloromethane/hexane to give N-(4-(phenylmethoxy)benzoyl)glycine methyl ester (14.75 g, 89%).

4. N-(4-(Phenylmethoxy)benzoyl)glycine pentafluorophenyl ester. N-(4-(Phenyl-methoxy)benzoyl)glycine methyl ester (14.75 g, 49.2 mmol) was boiled under reflux with methanolic sodium hydroxide (1M) (80 mL) for 2 h. The solvent was evaporated under reduced pressure. The residue was dissolved in water and was acidified by addition of aqueous hydrochloric acid. The suspension was extracted with ethyl acetate. The extract was washed with saturated brine and was dried with anhydrous magnesium sulphate. The solvent was evaporated under reduced pressure to give N-(4-(phenylmethoxy)benzoyl)glycine (6.59 g, 47%). Dicyclohexylcarbodiimide (720 mg, 3.5 mmol) was added to N-(4-(phenylmethoxy)benzoyl)glycine (100 g, 3.5 mmol) in dry tetrahydrofuran (100 mL) and the mixture was taken to 0° C. Pentafluorophenol (640 g, 3.5 mmol) was added dropwise and the mixture was stirred for 17 h at 0° C. The suspension was filtered and the solvent was evaporated from the filtrate under reduced pressure. The residue was dissolved in ethyl acetate (200 mL) and was washed with saturated aqueous sodium hydrogen carbonate (2×75 mL), with aqueous sulphuric acid (10%) and with water. The solution was dried with anhydrous magnesium sulphate and the solvent was evaporated under reduced pressure to give N-(4-(phenylmethoxy)benzoyl)glycine pentafluorophenyl ester (Intermediate B) (1.5 g, 95%).

Intermediate C 1. 1-(2-Nitroethenyl)-4-(phenylmethoxy)benzene. In a modification of the literature method [M. Hoequanx, B. Macot, G. Recleuith, C. Viel, M. Brunaub, J. Nauamo, C. Lacoun and C. Cozeubon, Diazoestrones and analogs. I. Pharmacological study and syntheses of heterosteroid analogs to establish structure—analgesic activity relationships, *Eur. J. Med. Chem.*, 1983, 19, 319–329], to 4-(phenylmethoxy)benzaldehyde (28 g, 132 mmol) in ethanol (900 mL) at 5° C. was added nitromethane (16.1 g, 264 mmol). Sodium hydroxide (13.2 g, 330 mmol) in ethanol (200 mL) was added dropwise and the mixture was stirred for 30 min at 5° C. The mixture was poured into a mixture of hydrochloric acid (9M; 136 mL) and water (208 mL). The precipitate was collected by filtration and was recrystallised from ethanol to give 1-(2-nitroethenyl)-4-(phenylmethoxy)benzene (14.0 g, 42%).

2. 2-(4-(Phenylmethoxy)phenyl)ethylamine. Lithium aluminium hydride (8.48 g, 223 mmol) was suspended in dry diethyl ether (600 mL). 1-(2-Nitroethenyl)-4(phenylmethoxy)benzene (13.9 g, 55 mmol) was extracted into this mixture using a Soxhlet apparatus. The mixture was boiled under reflux for 16 h. Water (7.38 mL) was added, followed by aqueous sodium hydroxide (20%; 5.53 mL) and water (27.8 mL). The suspension was filtered. The solvent was evaporated from the filtrate under reduced pressure to give 2-(4-(phenylmethoxy)phenyl)ethylamine (11.25 g, 91%).

Intermediate D

1. N-(1,1-Dimethylethoxycarbonyl)glycine N-(2-(4-phenylmethoxy)phenyl)ethyl)amide. N-(1,1-Dimethylethoxycarbonyl)glycine (850 mg, 4.85 mmol) was stirred with dicyclohexylcarbodiimide (1.00 g, 4.85 mmol) and 2-(4-(phenylmethoxy)phenyl)ethylamine (Intermediate C) (1.00 g, 4.4 mmol) in dry tetrahydrofuran (30 mL) for 16 h. The suspension was filtered and the solvent was evaporated from the filtrate under reduced pressure. The residue was dissolved in ethyl acetate and was washed with aqueous sulphuric acid (10%) and with saturated brine. The solution was dried with anhydrous magnesium sulphate and the solvent was evaporated under reduced pressure to give N-(1,1dimethylethoxycarbonyl)glycine N-(2-(-(phenylmethoxy)phenyl)ethyl)amide (1.65 g, 98%).

2. Glycine N-(2-(4-(phenylmethoxy)phenyl)ethyl)amide. N-(1,1-Dimethylethoxycarbonyl)glycine N-(2-(4-(phenyl)ethyl)amide (2.01 g, 5.23 mmol) was treated with excess hydrogen chloride in 1,4-dioxan (45 mL) for 2 h. The solid was collected by filtration and was dissolved in water and ethyl acetate. Aqueous sodium hydroxide was added to basify the solution to pH 9. The ethyl acetate solution was dried with anhydrous magnesium sulphate and the solvent was evaporated under reduce pressure to give glycine N-(2-(4-(phenylmethoxy)phenyl)ethyl)amide (1.15 g, 77%).

3. N-(N-(N-(1,1-Dimethylethoxycarbonyl)phenylalanyl)leucyl)glycine N-(2-(4-(phenylmethoxy)phenyl)ethyl)amide. N-(N-(1,1-Dimethylethoxycarbonyl)phenylalanyl)leucine pentafluorophenyl ester (1.19 g, 2.18 mmol) (Example A, Intermediate A) in tetrahydrofuran (30 mL) was added dropwise to glycine N-(2-(4-(phenylmethoxy)phenyl)ethyl)amide (620 mg, 2.18 mmol), N,N-diisopropylethylamine (310 mg, 2.4 mmol) and 1-hydroxybenzotriazole (20 mg) in tetrahydrofuran (30 mL) and the mixture was stirred for 16 h. The solvent was evaporated under reduced pressure. The residue, in ethyl acetate, was washed with aqueous sulphuric acid (10%) and with saturated aqueous sodium hydrogen carbonate. The solution was dried with anhydrous magnesium sulphate and the solvent was evaporated under reduced pressure. The residue was triturated with diethyl ether and the solid was collected by filtration to give N-(N-(N-(1,1-dimethylethoxycarbonyl)phenylalanyl)leucyl)glycine N-(2-(4-(phenylmethoxy)phenyl)ethyl)amide (360 mg, 26%) (Intermediate D).

Intermediate E

1. N-(1,1-Dimethylethoxycarbonyl)sarcosine 2,4,5-trichlorophenyl ester. N-(1,1-Dimethylethoxycarbonyl)sarcosine (10.0 g, 53 mmol) was stirred with 2,4,5-trichlorophenol (10.6 g, 53 mmol) and dicyclohexylcarbodiimide (10.9 g, 53 mmol) in ethyl acetate (100 mL) at −10° C. for 2.5 h. The suspension was filtered and the solvent was evaporated under reduced pressure from the filtrate. The residue was dissolved in ethyl acetate. The suspension was filtered and the solvent was evaporated under reduced pressure from the filtrate to give N-(1,1-dimethylethoxycarbonyl)sarcosine 2,4,5-trichlorophenyl ester (19.3 g, 98%).

2. N-(1,1-Dimethylethoxycarbonyl)sarcosine N-(2-aminoethyl)amide. N-(1,1-Dimethylethoxycarbonyl)sarcosine 2,4,5-trichlorophenyl ester (12.7 g, 34.5 mmol) in dichloromethane (50 mL) was added during 30 min to ethane-1,2-diamine (20.7 g, 345 mmol) in dichloromethane (150 mL) and the solution was stirred for a further 2 h. The solution was washed with water and with 10% aqueous sodium carbonate and was dried with anhydrous magnesium sulphate. The solvent was evaporated under reduced pressure to give N-(1,1-dimethylethoxycarbonyl)sarcosine N-(2-aminoethyl)amide (6.9 g, 86%).

3. Bis(2-(2-(N-(2-N-(1,1-Dimethylethoxycarbonyl)sarcosyl)aminoethyl)aminocarboxy)ethoxy)ethoxy)ethane. Bis(2-hydroxyethoxy)ethoxy)ethane (5.0 g, 21 mmol) was boiled in toluene (120 mL) for 20 h with azeotropic removal of water. The resulting solution was cooled to 20° C. Dichloromethane (35 mL) was added, followed by phosgene (1.93M in dichloromethane, 109 mL, 210 mmol). The solution was stirred for 4 h. The solvent and excess reagent were evaporated under reduced pressure from a portion (30 mL) of this solution to give crude bis(2-(2-(chlorocarboxy)ethoxy)ethoxy)ethane (900 mg, 2.5 mmol). This material was dissolved in dichloromethane (50 mL). To this solution was added triethylamine (1.26 g, 12.5 mmol) and 4-(dimethylamino)pyridine (20 mg). N-(1,1-dimethylethoxycarbonyl)sarcosine N-(2-aminoethyl)amide (1.73 g, 7.5 mmol) (Intermediate E2)in dichloromethane (100 mL) was then added dropwise during 40 min. The solution was stirred for 20 h before being washed with water, 10% aqueous sulphuric acid and water. The solution was dried with anhydrous magnesium sulphate and the solvent was evaporated under reduced pressure to give bis(2-(2-(N-(2-(N-(1,1-dimethylethoxycarbonyl)sarcosyl)aminoethyl)aminocarboxy)ethoxy)ethoxy)ethane (1.1 g, 59%).

4. Bis(2-(2-(N-(2-sarcosylaminoethyl)aminocarboxy)ethoxy)ethoxy)ethane dihydrochloride. Bis(2-(2-(N-(2-(N-(1,1-dimethylethoxycarbonyl)sarcosyl)aminoethyl)aminocarboxy)ethoxy)ethoxy)ethane (752 mg, 1 mmol) was treated with excess hydrogen chloride in dichloromethane for 2 h. Evaporation of the solvent gave bis(2-(2-(N-(2-sarcosylaminoethyl)aminocarboxy)ethoxy)ethoxy)ethane dihydro-chloride (550 mg, quantitative).

Preparation of the Peptide Portion of Example A

1. N-(N-Phenylalanylleucyl)glycine N-(2-(4-(phenylmethoxy)phenyl) ethyl)amide hydrochloride. N-(N-(1,1-Dimethylethoxycarbonyl)phenylalanylleucyl) glycine N-(2-(4-(phenylmethoxy) phenyl)ethyl)amide (3.89 g, 6.05 mmol) was treated with excess hydrogen chloride in dichloromethane (200 mL) for 3 h. The solvent and excess reagent were evaporated under reduced pressure. The residual oil was triturated with diethyl ether to give N-(N-phenylalanylleucyl)glycine N-(2-(4-(phenylmethoxy)phenyl)ethyl)amide hydrochloride (3.26 g, 93%).

2. N-(N-(N-(N-(4-(Phenylmethoxy)benzoyl)glycyl)phenylalanyl)leucyl)glycine N-(2-(4-(phenylmethoxy)phenyl)ethyl)amide. N-(N-Phenylalanylleucyl)g lycine N-(2-(4-(phenylmethoxy)phenyl)ethyl)amide hydrochloride (165 mg, 284 mol) was stirred with N,N-diisopropylethylamine (100 mg, 774 mol), 4-(dimethylamino)pyridine (10 mg) and 1-hydroxybenzotriazole (10 mg) in dry dichloromethane (5 mL) until all solid dissolved. N-(4-(Phenylmethoxy)benzoyl) glycine pentafluorophenyl ester (117 mg, 258 mol) (Example A, Intermediate B)in chloroform (10 mL) was added dropwise during 30 min and the reaction mixture was stirred for 5 h. The solvent was evaporated under reduced pressure. Column chromatography (silica gel; chloroform/methanol 50:1) of the residue gave N-(N-(N-(N-(4-(phenylmethoxy)benzoyl)glycyl)phenylalanyl)leucyl)glycine N-(2-(4-(phenylmethoxy)phenyl)ethyl)amide (170 mg, 81%).

3. N-(N-(N-(N-(4-Hydroxybenzoyl)glycyl)phenylalanyl)leucyl)glycine N-(2-(4-hydroxyphenyl)ethyl)amide. N-(N-(N-(N-(4-(Phenylmethoxy)benzoyl)glycyl)phenylalanyl)leucyl)glycine N-(2-(4-(phenylmethoxy)phenyl)ethyl)amide (444 mg, 547 mol) in ethanol (45 mL) was stirred vigorously with palladium on charcoal (10%; 50 mg) and hydrogen for 12 h. The suspension was filtered through diatomaceous earth. The solvent was evaporated from the filtrate under reduced pressure to give N-(N-(N-(N-(4-hydroxybenzoyl)glycyl)phenylalanyl)leucyl)glycine N-(2-(4-hydroxyphenyl)ethyl)amide (304 mg, 88%).

4. N-(N-(N-(N-(4-(Oxiranylmethoxy)benzoyl)glycyl) phenylalanyl)leucyl) glycine N-(2-(4-(oxiranylmethoxy)phenyl)ethyl)amide. N-(N-(N-(N-(4-Hydroxybenzoyl)glycyl)phenylalanyl)leucyl)glycine N-(2-(4-hydroxyphenyl) ethyl)amide (106 mg, 0.131 mol) was suspended in water (12 mL) containing sodium hydroxide (52.3 mg, 1.31 mmol). Chloromethyloxirane (604 mg, 6.5 mmol) in methanol (10 mL) was added, followed by phenylmethyltrimethylammonium hydroxide (40% aqueous solution, 90 mg). The solution was stirred for 48 h at 40° C. The solvent and excess reagent were evaporated under reduced pressure. The residue was dissolved in ethyl acetate and was washed with water. The solution was dried with anhydrous magnesium sulphate. The solvent was evaporated under reduced pressure. Column chromatography (silica gel; ethyl acetate, then ethyl acetate/methanol 39:1, then ethyl acetate/methanol 19:1, then ethyl acetate/methanol 9:1) gave N-(N-(N-(N-(4-(oxiranylmethoxy)benzoyl)glycyl) phenylalanyl)leucyl)glycine N-(2-(4-(oxiranylmethoxy)phenyl)ethyl)amide (26.5 mg, 27%).

5. Polymer A. It is contemplated that N-(N-(N-(N-(4-(Oxiranylmethoxy)benzoyl)glycyl)phenylalanyl)leucyl)glycine N-(2-(4-(oxiranylmethoxy)phenyl)ethyl)amide is boiled under reflux with anhydrous sodium carbonate and bis(2-(2-(N-(2-sarcosylaminoethyl)aminocarboxy)ethoxy)ethoxy)ethane dihydrochloride (Intermediate E) in ethanol for 6 h, giving the polymer of formula A.

Preparation of Peptide Portion of Example B

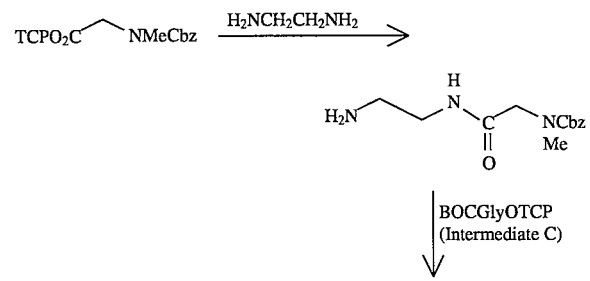

EXAMPLE B

PREPARATION OF INTERMEDIATES

Intermediate A

N-(1,1-Dimethylethoxycarbonyl)leucine 2,4,5-trichlorophenyl ester. N-(1,1-Dimethylethoxycarbonyl)leucine (6.32 g, 15 mmol) was stirred with 2,4,5-trichlorophenol (3.01 g, 15.2 mmol) and dicyclohexylcarbodiimide (3.14 g, 15.2 mmol) in ethyl acetate (50 mL) at $-10°$ C. for 4 h. The suspension was filtered and the solvent was evaporated under reduced pressure from the filtrate. The residue was dissolved in ethyl acetate. The suspension was filtered and the solvent was evaporated under reduced pressure from the filtrate to give N-(1,1-dimethylethoxycarbonyl)leucine 2,4, 5-trichlorophenyl ester (6.2 g, 99%).

Intermediate B

N-(1,1-Dimethylethoxycarbonyl)phenylalanine pentafluorophenyl ester. N-(1,1-Dimethylethoxycarbonyl)phenylalanine (6.36 g, 24 mmol) in ethyl acetate (50 mL) at $0°$ C. was added to dicyclohexylcarbodiimide (4.95 g, 24 mmol) and pentafluorophenol (4.42 g, 24 mmol) in ethyl acetate (50 mL) at $0°$ C. The mixture was stirred for 2.75 h at $0°$ C. The suspension was filtered and the solvent was evaporated under reduced pressure from the filtrate. The residue was dissolved in ethyl acetate. The suspension was filtered and the solvent was evaporated under reduced pressure from the filtrate to give N-(1,1-dimethylethoxycarbonyl)phenylalanine pentafluorophenyl ester (10.32 g, quantitative).

Intermediate C

N-(1,1-Dimethylethoxycarbonyl)glycine 2,4,5-trichlorophenyl ester. N-(1,1-Dimethylethoxycarbonyl)glycine (6.12 g, 35 mmol) was stirred with 2,4,5-trichlorophenol (6.91 g, 35 mmol) and dicyclohexylcarbodiimide (7.22 g, 35 mmol) in ethyl acetate (100 mL) at $0°$ C. for 4 h. The suspension was filtered and the solvent was evaporated under reduced pressure from the filtrate. The residue was

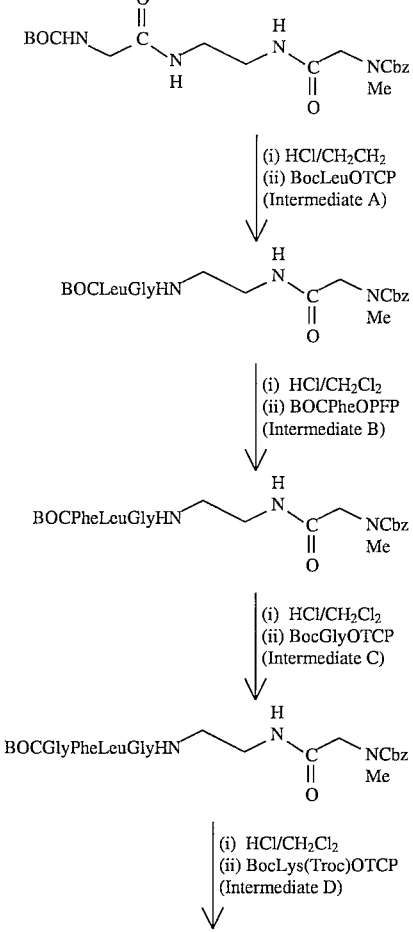

Preparation of Peptide Portion of Example B

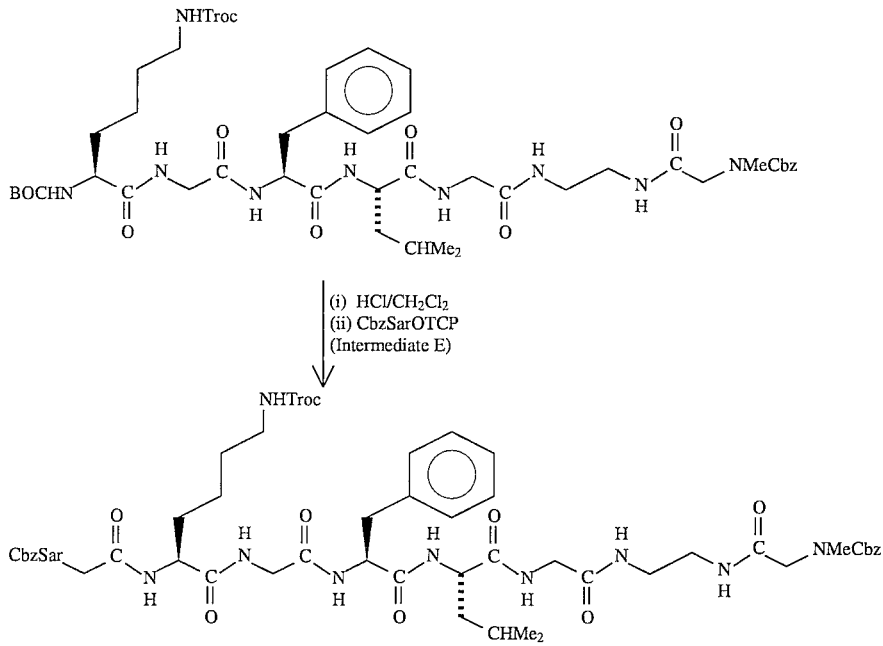

dissolved in ethyl acetate. The suspension was filtered and the solvent was evaporated under reduced pressure from the filtrate to give N-(1,1-dimethylethoxycarbonyl)glycine 2,4,5-trichlorophenyl ester (12.4 g, quantitative).

Intermediate D

1. $N^\alpha$-(1,1-Dimethylethoxycarbonyl)-$N^\epsilon$-(2,2,2-trichloroethoxycarbonyl)lysine. In a modification of a literature method [Yajima, H.; Watanabe, H.; Okamoto, M., Studies on peptides. XXXIII. $N^\epsilon$-β,β,β-Trichloroethyloxycarbonyllysine, *Chem. Pharm. Bull*, 1971, 19, 2185–2189], lysine monohydrochloride (9.14 g, 50 mmol) was stirred under reflux with copper (II) carbonate (21.6 g, 75 mmol) in water (180 mL) for 3 h. The solution was filtered while hot and the filtrate was cooled to 20° C. 2,2,2-Trichloroethyl chloroformate (15.9 g, 75 mmol) and aqueous sodium carbonate (13.3 g, 125 mmol in 40 mL) were added alternately in portions to the filtrate during 30 min and the mixture was stirred vigorously at 0° C. for 20 h. The blue precipitate was collected and was boiled under reflux with ethylenediaminetetraacetic acid disodium salt (18.6 g, 100 mmol) in water (200 mL) for 2 h. The solution was cooled to 0° C. for 20 hrs and crude $N^\epsilon$-(2,2,2-trichloroethoxycarbonyl)lysine was collected as a gummy solid. This material was dissolved in water (75 mL) and triethylamine (20.2 g, 200 mmol) was added, followed by di-t-butyl dicarbonate (13.64 g, 62 mmol) and 1,4-dioxan (30 mL). The mixture was stirred vigorously for 3 d. The mixture was washed with diethyl ether. Ethyl acetate was added to the aqueous phase and the mixture was acidified by careful addition of cold 10% aqueous sulphuric acid. The ethyl acetate phase was washed with water and dried with anhydrous magnesium sulphate. The solvent was evaporated under reduced pressure to give $N^\alpha$-(1,1-dimethylethoxycarbonyl)-$N^\epsilon$-(2,2,2-trichloroethoxycarbonyl)lysine (12.32 g, 55%).

2. $N^\alpha$-(1,1-Dimethylethoxycarbonyl)-$N^\epsilon$-(2,2,2-trichloroethoxycarbonyl)lysine 2,4,5-trichlorophenyl ester. $N^\alpha$-(1,1-Dimethylethoxycarbonyl)-$N^\epsilon$-(2,2,2-trichloroethoxy-carbonyl)lysine (6.32 g, 15 mmol) was stirred with 2,4,5-trichlorophenol (2.96 g, 15 mmol) and dicyclohexylcarbodiimide (3.10 g, 15 mmol) in ethyl acetate (100 mL) at 0° C. for 20 h. The suspension was filtered and the solvent was evaporated under reduced pressure from the filtrate. The residue was dissolved in ethyl acetate. The suspension was filtered and the solvent was evaporated under reduced pressure from the filtrate to give $N^\alpha$-(1,1-dimethylethoxycarbonyl)-$N^\epsilon$-(2,2,2-trichloroethoxy-carbonyl)lysine 2,4,5-trichlorophenylester (7.50 g, 97%).

Intermediate E

1. N-(Phenylmethoxycarbonyl)sarcosine 2,4,5-trichlorophenylester. N-(Phenylmethoxycarbonyl)sarcosine (4.0 g, 18 mmol) was stirred with 2,4,5-trichlorophenol (3.53 g, 18 mmol) and dicyclohexylcarbodiimide (3.69 g, 18 mmol) in ethyl acetate (40 mL) at −10° C. for 1 h, then at 20° C. for 20 h. The suspension was cooled to 0° C. The suspension was filtered and the solvent was evaporated under reduced pressure from the filtrate. The residue was dissolved in ethyl acetate. The suspension was filtered and the solvent was evaporated under reduced pressure from the filtrate to give N-(phenylmethoxycarbonyl)sarcosine 2,4,5-trichlorophenyl ester (7.2 g, quantitative).

2. N-(Phenymethoxycarbonyl)sarcosine pentafluorophenyl ester. N-(Phenylmethoxycarbonyl)sarcosine (3.0 g, 13.4 mmol) was stirred with pentafluorophenol (2.46 g, 13.4 mmol) and dicyclohexylcarbodiimide (2.32 g, 13.4 mmol) in ethyl acetate (30 mL) at 0° C. for 2 h. The suspension was filtered and the solvent was evaporated under reduced pressure from the filtrate. The residue was dissolved in ethyl acetate. The suspension was filtered and the solvent was evaporated under reduced pressure from the filtrate to give N-(phenylmethoxycarbonyl)sarcosine pentafluorophenyl ester (4.66 g, 89%).

Intermediate F 1. 5-(4-Nitrophenyl)-10,15,20-triphenyl-21H,23H-porphine. Fuming nitric acid (density 1.5 mL$^{-1}$) (2.26 mL) was added during 2 h to 5,10,15,20-tetraphenyl-21H,23H-porphine (2.00 g, 3.26 mmol) in chloroform (ethanol-free) (300 mL). The mixture was washed with water (5×300 mL) and was dried with anhydrous sodium carbonate and anhydrous magnesium sulphate. The solvent was evaporated under reduced pressure. Chromatography (silica gel; dichloromethane/hexane 2:1) of the residue gave 5-(4-nitrophenyl)-10,15,20-triphenyl-21H,23H-porphine (1.17 g, 55%).

2. 4-(10,15,20-Triphenyl-21H,23H-porphin-5-yl)benzeneamine. Tin(II) chloride dihydrate (595 mg, 2.6 mmol) was added to 5-(4-nitrophenyl)-10,15,20-triphenyl-21H,23H-porphine (580 mg, 0.88 mmol) in aqueous hydrochloric acid (9M. 20 mL) and the mixture was stirred at 65° C. for 2 h. The solution was allowed to cool and was added to water (70 mL). Concentrated aqueous ammonia was added until the solution was basified to pH 8. The suspension was extracted with chloroform (9×75 mL). The chloroform fractions were combined and were dried with anhydrous magnesium sulphate. The solvent was evaporated under reduced pressure. Chromatography (silica gel; dichloromethane/hexane 5:1) of the residue gave 4-(10,15,20-triphenyl-21H,23H-porphin-5-yl)benzeneamine (462 mg, 84%).

3. 4-Oxo-4-(4-(10,15,20-triphenyl-21H,23H-porphin-5-yl)phenylamino)butanoic acid. 4-(10,15,20-Triphenyl-21H, 23H-porphin-5-yl)benzeneamine (450 mg, 0.72 mmol) was dissolved in chloroform (ethanol-free) (10 mL) with warming. Succinic anhydride (tetrahydrofuran-2,5-dione) (64 mg, 0.72 mmol) was added and the mixture was boiled under reflux for 2.5 h. A further portion of succinic anhydride (32 mg, 0.36 mmol) was added and boiling under reflux continued for a further 2 h. The mixture was cooled to ambient temperature for 16 h. The precipitated solid was collected by filtration to give 4-oxo-4-(4-(10,15,20-triphenyl-21H,23H-porphin-5-yl)phenylamino)butanoic acid (460 mg, 89%).

Preparation of Peptide Portion of Example B

1. N-(Phenylmethoxycarbonyl)sarcosine N-(2-aminoethyl)amide. N-(Phenylmethoxycarbonyl)sarcosine pentafluorophenyl ester (3.5 g, 9.2 mmol) in dichloromethane (40 mL) was added during 30 min to ethane-1,2-diamine (10.8 g, 180 mmol) in dichloromethane (300 mL) and the solution was stirred for a further 2 h. The solution was washed with water and with 10% aqueous sodium carbonate and was dried with anhydrous magnesium sulphate. The solvent was evaporated under reduced pressure to give N-(phenylmethoxycarbonyl)sarcosine N-(2-aminoethyl)amide (2.1 g, 88%). This material was also prepared similarly from N-(phenylmethoxycarbonyl)sarcosine 2,4,5-trichlorophenyl ester.

2. N-(1,1-Dimethylethoxycarbonyl)glycine N-(2-(N-phenylmethoxycarbonyl)sarcosylamino)ethyl)amide. N-(Phenylmethoxycarbonyl)sarcosine N-(2-aminoethyl)amide (3.71 g, 14 mmol) was stirred with N-(1,1-dimethylethoxycarbonyl)glycine 2,4,5-trichlorophenyl ester (4.96 g, 14 mmol, Example B, Intermediate C) and N,N-diisopropylethylamine (1.99 g, 15.4 mmol) in dichloromethane (100 mL) for 20 h. The solution was washed with cold 10% aqueous sulphuric acid (2×) and with saturated aqueous sodium hydrogen carbonate and was dried with anhydrous magnesium sulphate. The solvent was evaporated under reduced pressure. Chromatography (silica gel; ethyl acetate/methanol 10:1, then ethyl acetate/methanol 5:1, then ethyl acetate/methanol 3:1) of the residue gave N-(1,1-dimethylethoxycarbonyl)glycine N-(2-(N-phenylmethoxycarbonyl)sarcosylamino)ethyl)amide (2.12 g, 37%).

3. Glycine N-(2-(N-phenylmethoxycarbonyl)sarcosylamino)ethyl)amide hydrochloride. N-(1,1-Dimethylethoxycarbonyl)glycine N-(2-(N-phenylmethoxycarbonyl)sarcosylamino)ethyl)amide (2.04 g, 4.95 mmol) was treated with excess hydrogen chloride in dichloromethane (50 mL) for 1 h. The solvent and excess reagent were evaporated under reduced pressure to give glycine N-(2-(N-phenylmethoxycarbonyl)sarcosylamino)ethyl)amide hydrochloride (1.5 g, quantitative).

4. N-(N-(1,1-Dimethylethoxycarbonyl)leucyl)glycine N-(2-(N-(phenylmethoxycarbonyl)sarcosylamino)ethyl)amide. N-(1,1-Dimethylethoxycarbonyl)glycine N-(2-(N-(phenylmethoxycarbonyl)sarcosylamino)ethyl)amide (5.22 g, 8 mmol) was treated with excess hydrogen chloride in dichloromethane (50 mL) for 1 h. Water (50 mL) was added and the mixture was stirred vigorously for 15 min. The solvent and excess reagent were evaporated from the aqueous layer under reduced pressure to give crude glycine N-(2-(N-(phenylmethoxycarbonyl)sarcosylamino)ethyl)amide hydrochloride as a white solid. This material was stirred with N,N-diisopropylethylamine (3.231 g, 25 mmol) and N-(1,1-dimethylethoxycarbonyl)leucine 2,4,5-trichlorophenyl ester (3.19 g, 7.8 mmol) (Example II, Intermediate A) in dimethylformamide (30 mL) for 3 d. The solvent was evaporated under reduced pressure. The residue was dissolved in ethyl acetate and was washed with aqueous sodium hydroxide (5%), aqueous sulphuric acid (10%) and water and was dried with anhydrous magnesium sulphate. Evaporation of the solvent under reduced pressure gave N-(N-(1,1-dimethylethoxycarbonyl)leucyl)glycine N-(2-(N-(phenylmethoxycarbonyl)sarcosylamino)ethyl)amide (3.26 g, 78%).

5. N-Leucylglycine N-(2-(N-(phenylmethoxycarbonyl)sarcosylamino)ethyl)amide hydrochloride. N-(N-(1,1-Dimethylethoxycarbonyl)leucyl)glycine N-(2-(N-(phenylmethoxycarbonyl)sarcosylamino)ethyl)amide (3.26 g, 6.1 mmol) was treated with excess hydrogen chloride in dichloromethane (40 mL) for 1 h. The solvent and excess reagent were evaporated under reduced pressure to give N-leucylglycine N-(2-(N-(phenylmethoxycarbonyl)sarcosylamino)ethyl)amide hydrochloride (2.65 g, quantitative).

6. N-(N-(N-(1,1-Dimethylethoxycarbonyl)phenylalanyl)leucyl)glycine N-(2-(N-(phenylmethoxycarbonyl)sarcosylamino)ethyl) amide. N-(1,1-Dimethylethoxycarbonyl)phenylalanine pentafluorophenyl ester (2.65 g, 6.1 mmol) (Example B, Intermediate B) was added to N-leucylglycine N-(2-(N-(phenylmethoxycarbonyl)sarcosylamino)ethyl)amide hydrochloride (2.81 g, 6.16 mmol), N-N-diisopropylethylamine (1.75 g, 13.5 mmol) and 4-(dimethylamino)pyridine (10 mg) in dichloromethane (30 mL) and the mixture was stirred for 2 d. The solution was then washed with cold aqueous sulphuric acid (10%), aqueous sodium carbonate (10%) and saturated brine. The solution was dried with anhydrous magnesium sulphate and the solvent was evaporated under reduced pressure. Chromatography (silica gel; chloroform/methanol 1:1) gave N-(N-(N-(1,1-dimethylethoxycarbonyl)phenylalanyl)leucyl)glycine N-(2-(N(phenylmethoxycarbonyl)sarcosylamino)ethyl)amide (1.94 g, 46%).

7. N-(N-Phenylalanylleucyl)glycine N-(2-(N-(phenylmethoxycarbonyl)sarcosylamino)ethylamyi-dehydrochloride. N-(N-(N-(1,1-Dimethylethoxycarbonyl)phenylalanyl)leucyl)glycine N-(2-(N-(phenylmethoxycarbonyl)sarcosylamino)ethyl)amide (1.94 g, 2.8 mmol) was treated with excess hydrogen chloride in dichloromethane (25 mL) for 1 h. The solvent and excess reagent were evaporated under reduced pressure. The residue was dissolved in methanol. Evaporation of the solvent under reduced pressure gave N-(N-phenylalanylleucyl)glycine N-(2-(N-(phenylmethoxycarbonyl)sarcosylamino)ethyl)amide hydrochloride (1.67 g, 95%).

8. N-(N-(N-(N-(1,1-Dimethylethoxycarbonyl)glycyl)phenylalanyl)leucyl)glycine N-(2-(N-(phenylmethoxycarbonyl)sarcosylamino)ethyl)amide. N-(1,1-Dimethylethoxycarbonyl)glycine 2,4,5-trichlorophenyl ester (1.58 g, 2.55 mmol) (Example B, Intermediate C) and 4-(dimethylamino)pyridine (3.1 g, 2.5 mmol) were added to N-(N-phenylalanylleucyl)glycine N-(2-(N(phenylmethoxycarbonyl)sarcosylamino)ethyl)amide hydrochloride (904 mg, 2.55 mmol) and N,N-diisopropylethylamine (990 mg, 7.7 mmol) in dichloromethane (20 mL). The mixture was stirred for 4 d. The solution was washed with cold aqueous sulphuric acid (10%), aqueous sodium carbonate (10%) and saturated brine. The solution was dried with anhydrous magnesium sulphate and the solvent was evaporated under reduced pressure. Chromatography (silica gel; chloroform, then chloroform/methanol 10:1) of the residue gave N-(N-(N-(N-(1,1-dimethylethoxycarbonyl)glycyl)phenylalanyl)leucyl)glycine N-(2-(N(phenylmethoxycarbonyl)sarcosylamino)ethyl)amide (1.14 g, 61%).

9. N-(N-(N-glycylphenylalanyl)leucyl)glycine N-(2-(N-(phenylmethoxycarbonyl)sarcosylamino)ethyl)amide hydrochloride. N-(N-(N-(N-(1,1 -Dimethylethoxycarbonyl)glycyl)phenylalanyl)leucyl)glycine N-(2-(N-(phenylmethoxycarbonyl)sarcosylamino)ethyl)amide (1.29 g, 1.77 mmol) was treated with excess hydrogen chloride in dichloromethane (10 mL) for 1 h. Methanol (1 mL) was added and the solvents and excess reagents were evaporated under reduced pressure to give N-(N-(N-glycylphenylalanyl)leucyl)glycine N-(2-(N-(phenylmethoxycarbonyl)sarcosylamino)ethyl)amide hydrochloride (1.1 g, quantitative).

10. N-(N-(N-(N-(N$^\alpha$-(1,1-Dimethylethoxycarbonyl)-N$^\epsilon$-(2,2,2-trichloroethoxycarbonyl)lysyl)glycyl) phenylalanyl)leucyl)glycine N-(2-(N-(phenylmethoxy-carbonyl)sarcosyl-amino)ethyl)amide. N-(N-(N-Glycylphenylalanyl)leucyl)glycine N-(2-(N-(phenylmethoxycarbonyl)sarcosylamino)ethyl)amide hydrochloride (1.11 g, 1.77 mmol) was added to N,N-diisopropylethylamine (683 mg, 5.3 mmol) in dichloromethane (10 mL). To this mixture was added N$^\alpha$-(1,1-dimethylethoxycarbonyl)-N$^\epsilon$-(2,2,2-trichloroethoxycarbonyl)lysine 2,4,5-trichlorophenyl ester (950 mg, 1.77 mmol) (Example B, Intermediate D) in dichloromethane (20 mL) and 4-(dimethylamino)pyridine (10 mg). The mixture was stirred for 3 d. The solution was washed with cold aqueous sulphuric acid (10%), aqueous sodium carbonate (10%) and saturated brine. The solution was dried with anhydrous magnesium sulphate and the solvent was evaporated under reduced pressure. Chromatography (silica gel; chloroform, then chloroform/methanol 10:1) of the residue gave N-(N-(N-(N-(N$^\alpha$-(1,1-dimethylethoxycarbonyl)-N$^\epsilon$-(2,2,2-trichloroethoxycarbonyl)lysyl)glycyl)phenylalanyl)leucyl)glycine N-(2-(N-(phenylmethoxycarbonyl)sarcosylamino)ethyl)amide. (1.44 g, 78%).

11. N-(N-(N-(N-(N$^\epsilon$-(2,2,2-Trichloroethoxycarbonyl)lysyl)glycyl)phenylalanyl)leucyl)glycine N-(2-(N-(phenylmethoxycarbonyl)sarcosylamino)ethyl)amide hydrochloride. N-(N-(N-(N-(N$^\alpha$-(1,1-Dimethylethoxycarbonyl)-N$^\epsilon$-(2,2,2-trichloroethoxycarbonyl)lysyl)glycyl)phenylalanyl)leucyl)glycine N-(2-(N-(phenylmethoxycarbonyl)sarcosylamino)ethyl)amide (1.32 g, 1.27 mmol) was treated with excess hydrogen chloride in dichloromethane (20 mL) for 1 h. Methanol (1.0 mL) was added and the mixture was filtered. The solvent was evaporated from the filtrate under reduced pressure to give N-(N-(N-(N-(N$^\epsilon$-(2,2,2-trichloroethoxycarbonyl)lysyl)glycyl)phenylalanyl)leucyl)glycine N-(2-(N(phenylmethoxycarbonyl)sarcosylamino)ethyl)amide hydrochloride (1.14 g, 92%).

12. N-(N-(N-(N-(N$^\alpha$-(N-(Phenylmethoxycarbonyl)sarcosyl)-N$^\epsilon$-(2,2,2-trichloroethoxycarbonyl) lysyl)glycyl)phenylalanyl)-leucyl)glycine N-(2-(N-(phenylmethoxycarbonyl)sarcosyl-amino)ethyl)amide. N-(N-(N-(N-(N$^\epsilon$-(2,2,2-Trichloroethoxycarbonyl)lysyl)glycyl)phenylalanyl)leucyl)glycine N-(2-(N(phenylmethoxycarbonyl)sarcosylamino)ethyl)amide hydrochloride (980 mg, 1.0 mmol) was stirred with N,N-diisopropylethylamine (402 mg, 3.1 mmol), N-(phenylmethoxycarbonyl)sarcosine 2,4,5-trichlorophenyl ester (418 mg, 1.0 mmol) (Example B, Intermediate E) and 4-(dimethylamino)pyridine (10 mg) in dichloromethane (30 mL) for 24 h. The solution was washed with saturated aqueous sodium hydrogen carbonate and with aqueous sulphuric acid (2M) and was dried with anhydrous magnesium sulphate. The solvent was evaporated under reduced pressure. Chromatography (silica gel, chloroform/methanol 20:1, then chloroform/methanol 10:1) of the residue gave N-(N-(N-(N-(N$^\alpha$-(N-(phenylmethoxycarbonyl)sarcosyl)-N$^\epsilon$-(2,2,2-trichloroethoxycarbonyl)lysyl)glycyl)phenylalanyl)leucyl)glycine N-(2-(N-(phenylmethoxycarbonyl)sarcosylamino)ethyl)amide (418 mg, 36%).

13. N-(N-(N-(N-(N$^\alpha$-(N-(Phenylmethoxycarbonyl)sarcosyl)lysyl)glycyl)phenylalanyl)leucyl)glycine N-(2-(N-(phenylmethoxycarbonyl)sarcosylamino)ethyl)amide. It is contemplated that N-(N-(N-(N-(N$^\alpha$-(N-(Phenylmethoxycarbonyl)sarcosyl)-N$^\epsilon$-(2,2,2-trichloroethoxycarbonyl)lysyl)glycyl)phenylalanyl)leucyl)glycine N-(2-(N-(phenylmethoxycarbonyl)sarcosylamino) ethyl)amide is boiled under reflux with zinc powder in methanol for 2 h. The solvent is evaporated under reduced pressure. Ethyl acetate is added to the residue. The suspension is filtered and the filtrate is washed with twice with water. The solution is dried with anhydrous magnesium sulphate and the solvent is evaporated under reduced pressure to give N-(N-(N-(N-(N$^\alpha$(N-(phenylmethoxycarbonyl)sarcosyl)lysyl)glycyl)phenylalanyl) leucyl)glycine N-(2-(N-(phenylmethoxycarbonyl)sarcosylamino)ethyl)amide.

14. N-(N-(N-(N-(N-(N-(Phenylmethoxycarbonyl)sarcosyl)-N-(4-oxo-4-(4-(10,15,20-triphenyl-21H,23H-porphin-5-yl)phenylamino)butanoyl)lysyl)glycyl)phenylalanyl)leucyl)glycine N-(2-(N-(phenylmethoxycarbonyl)sarcosylamino)ethyl)amide. It is contemplated that 4-oxo-4-(4-(10,15,20-triphenyl-21H, 23H-porphin-5-yl)phenylamino)butanoic acid (Example B Intermediate E 3) is stirred with pentafluorophenol and dicyclohexylcarbodiimide in dimethylformamide for 16 h at 4° C. The suspension is filtered and the filtrate was added to N-(N-(N-(N-(N-(N(phenylmethoxycarbonyl)sarcosyl)lysyl)glycyl)phenylalanyl)leucyl)glycine N-(2-(N(phenylmethoxycarbonyl)sarcosylamino)ethyl)amide and 4-(dimethylamino) pyridine in tetrahydrofuran. The mixture is stirred for 2 d. Ethyl acetate is added and the solution is washed thrice with water, twice with 10% aqueous sodium carbonate solution and once with saturated brine. The solution is dried with anhydrous magnesium sulphate and the solvent is evaporated under reduced pressure. Chromatography (silica gel) of the residue gives N-(N-(N-(N-(N-(N-(phenylmethoxycarbonyl)sarcosyl)-N-(4-oxo-4-(4-(10,15, 20-triphenyl-21H,23H-porphin-5-yl)phenylamino)butanoyl)lysyl)glycyl)phenylalanyl)leucyl)glycine N-(2-(N(phenylmethoxycarbonyl)sarcosylamino)ethyl)amide.

15. N-(N-(N-(N-(N-Sarcosyl-N-(4-oxo-4-(4-(10,15,20-triphenyl-21H,23H-porphin-5-yl) phenylamino)butanoyl)lysyl)glycyl)phenylalanyl)leucyl)glycine N-(2-sarcosylaminoethyl)amide dihydrobromide. It is contemplated that N-(N-(N-(N-(N-(N-(Phenylmethoxycarbonyl)sarcosyl)-N-(4-oxo-4-(4-(10,15,20-triphenyl-21H,23H-porphin-5-yl)phenylamino)butanoyl)lysyl)glycyl)phenylalanyl)leucyl)glycine N-(2-(N-(phenylmethoxycarbonyl)sarcosylamino)ethyl)amide is stirred with 30% hydrogen bromide in acetic acid for 1 h. The solvent and excess reagent is evaporated under reduced pressure. Trituration of the residue with five portions of dry diethyl ether give N-(N-(N-(N-(N-sarcosyl-N-(4-oxo-4-(4-(10,15,20-triphenyl-21H,23H-porphin-5-yl)phenylamino)butanoyl) lysyl)glycyl)phenylalanyl)leucyl)glycine N-(2-sarcosylaminoethyl)amide dihydrobromide.

16. Polymer B. It is contemplated that N-(N-(N-(N-(N-Sarcosyl-N-(4-oxo-4-(4-(10,15,20-triphenyl-21H,23H-porphin-5-yl)phenylamino)butanoyl)lysyl)glycyl)phenylalanyl)leucyl)glycine N-(2-sarcosylaminoethyl)amide dihydrobromide is boiled under reflux with anhydrous sodium carbonate and poly(oxyethylene)-,-bis(oxiranylmethyl) ether (prepared by the literature method [Y. Chen and M. Feng, Chinese Patent 86 104 089, 1987]) in ethanol for 6 h. The suspension is filtered and the solvent is evaporated from the filtrate under reduced pressure to give the polymer.

Actual levels of active ingredient in administered compositions of the present invention may be varied so as to obtain an amount of active ingredient that is effective to obtain the desired effect for a particular composition and method of administration. The selected dosage level therefore depends upon the desired effect, on the route of administration, on the desired duration of treatment and other commonly considered factors.

The total daily dose of the compounds of this invention administered to a host in single or divided dose may be in amounts, for example, of from about 1 picomol to about 10 millimoles of cytotoxic agent per kilogram of body weight. Dosage unit compositions may contain such amounts or such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The dosages of the contrast agent used according to the method of the present invention will vary according to the precise nature of the contrast agent used. Preferably however, the dosage should be kept as low as is consistent with achieving contrast enhanced imaging and volumes minimized for IV drip or bolus injection. In this way, the toxicity potential is minimized. For most contrast agents the appropriate dosage will generally range from 0.02 to 3 mmol paramagnetic metal/kg body weight, especially 0.05 to 1.5 mmol/kg, particularly 0.08 to 0.5, more especially 0.1 to 0.4 mmol/kg. It is well within the skill of the average practitioner in this field to determine the optimum dosage for any particular contrast agent for both in vivo or in vitro applications.

Contrast agents may be formulated with conventional pharmaceutical or veterinary aids, for example stabilizers, antioxidants, osmolality adjusting agents, buffers, pH adjusting agents, etc.., and may be in a form suitable for injection or infusion directly or after dispersion in or dilution with a physiologically acceptable carrier medium, e.g., water for injection. Thus the contrast agents may be formulated in conventional administration forms such as powders, solutions, suspensions, dispersions, etc., however solutions, suspensions and dispersions in physiologically acceptable carrier media will generally be preferred.

The contrast agents may be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

Parenterally administrable forms, e.g., intravenous solutions, should of course be sterile and free from physiologically unacceptable agents, and should have low osmolality to minimize irritation or other adverse effects upon administration. Thus, the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in *Remington's Pharmaceutical Sciences,* 15th ed., Easton: Mack Publishing Co., pp. 1405–1412 and 1461–1487 (1975) and *The National Formulary XIV,* 14th ed. Washington: American Pharmaceutical Association (1975). The solutions can contain preservatives, antimicrobial agents, buffers and antioxidants conventionally used for parenteral solutions, excipients and other additives which are compatible with the contrast agents and which will not interfere with the manufacture, storage or use of products.

The present invention includes one or more of the polymers of this invention formulated into compositions together with one or more non-toxic physiologically acceptable carriers, adjuvants or vehicles which are collectively referred to herein as carriers, for parenteral injection, for oral administration in solid or liquid form, for rectal or topical administration, or the like.

The compositions can be administered to humans and animals either orally, rectally, parenterally (intravenous, intramuscularly or subcutaneously), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders and lyophilizates for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, cryoprotecting, and dispensing agents. Prevention of the action of microorganisms can be ensured by various antibacterial and antifungal agents, for example, parabens, chlorobutanol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glylcerol, (d) disintegrating agents, as for example, agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar and tragacanth, or mixtures of these substances, and the like.

Compositions for rectal or vaginal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays and inhalants. The active component is admixed under sterile conditions with a physiologically acceptable carrier and any preservatives, buffers or propellants as may be required. Opthalmic formulations, eye ointments, powders and solutions are also contemplated as being within the scope of this invention.

We claim:

1. A linear block copolymer comprising units of an alkylene oxide, linked to units of peptide via a linking group comprising a —$CH_2CHOHCH_2(N)R$— moiety, wherein R is $C_{1-4}$ alkyl group.

2. A linear block copolymer, according to claim 1, wherein the linking group is selected from the group consisting of:

—$CONH(CH_2)_pNHCOCH_2N(CH_3)CH_2CHOHCH_2OC_6H_4$—;

—$CONH(CH_2)_pNHCOCH_2N(CH_3)CH_2CHOHCH_2OC_6H_4CO$—;

—$CONH(CH_2)pNHCOCH_2N(CH_3)CH_2CHOHCH_2OC_6H_4(CH_2)_2$—;

—$CONH(CH_2)_pNHCOCH_2N(CH_3)CH_2CHOHCH_2OC_6H_4(CH_2)_2NH$—;

—$NH(CH_2)_pN(CH_3)CH_2CHOHCH_2OC_6H_4$—;

—$NH(CH_2)_pN(CH_3)CH_2CHOHCH_2OC_6H_4CO$—;

—$NH(CH_2)_pN(CH_3)CH_2CHOHCH_2OC_6H_4(CH_2)_2$—;

—$NH(CH_2)_pN(CH_3)CH_2CHOHCH_2OC_6H_4(CH_2)_2NH$—;

—$CONH(CH_2)_pNHCO(CH_2)pN(CH_3)CH_2CHOHCH_2$—;

—$NH(CH_2)_pNHCO(CH_2)pN(CH_3)CH_2CHOHCH_2$—;

—$NHCO(CH_2)_pN(CH_3)CH_2CHOHCH_2$—; and

—$CO(CH_2)_pN(CH_3)CH_2CHOHCH_2$— wherein p is 1–6.

3. A copolymer according to claim 2 wherein the peptide is of about 3 to about 50 amino acids in length.

4. A copolymer according to claim 2 wherein the units of alkylene oxide are units of ethylene oxide.

5. A copolymer according to claim 3 wherein the units of alkylene oxide are units of ethylene oxide.

6. A copolymer according to claim 2 wherein the molecular weight is 10,000 to 1 million.

7. A prodrug or drug in a copolymer according to claim 6.

8. A passive targeting copolymer according to claim 6.

9. A copolymer according to claim 6, wherein the peptide is derivatized with a metal chelating agent.

10. A copolymer according to claim 9 wherein the chelating agent has a metal associated therewith.

11. A copolymer according to claim 10 wherein the metal is paramagnetic.

12. A diagnostic imaging copolymer according to claim 11.

13. A copolymer according to claim 10 wherein the metal is a radionuclide.

14. A cytotoxic copolymer according to claim 13.

15. A copolymer according to claim 14 having a molecular weight of 70 kd to 80 kd.

16. A block copolymer according to claim 1 selected from the group consisting of;

—(PAG)N(R)$CH_2CHOHCH_2OC_6H_4$CO(peptide)NH$(CH_2)_pC_6H_4$O$CH_2CHOHCH_2$N(R)— and —(PAG)$CH_2CHOHCH_2$N(R)$CH_2$CO(Peptide)NH$(CH_2)_p$NHCO$CH_2$N(R)$CH_2CHOHCH_2$ wherein R is a 1–4 carbon alkyl group;

p is from 1 to 6;

PAG is polyethylene oxide; and the peptide is Gly-Phe-Leu-Gly; or Lys-Gly-Phe-Leu-Gly.

17. The process of preparing a polymer according to claim 1 by reacting a bis(epoxide) reagent with a bis(amine) reagent, wherein one of said reagents incorporates said peptide units and the other reagent incorporates said alkylene oxide units.

* * * * *